(12) United States Patent
Snow et al.

(10) Patent No.: US 11,793,498 B2
(45) Date of Patent: Oct. 24, 2023

(54) BIOPSY NEEDLE DEVICES AND METHODS OF USE

(71) Applicant: Merit Medical Systems, Inc., South Jordan, UT (US)

(72) Inventors: Jeremy Snow, South Jordan, UT (US); Jacob Forman, West Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 72 days.

(21) Appl. No.: 15/982,777

(22) Filed: May 17, 2018

(65) Prior Publication Data

US 2018/0333147 A1 Nov. 22, 2018

Related U.S. Application Data

(60) Provisional application No. 62/508,797, filed on May 19, 2017.

(51) Int. Cl.
*A61B 10/02* (2006.01)

(52) U.S. Cl.
CPC .. *A61B 10/0275* (2013.01); *A61B 2010/0208* (2013.01)

(58) Field of Classification Search
None
See application file for complete search history.

(56) References Cited

U.S. PATENT DOCUMENTS

| 737,293 | A | 8/1903 | Summerfeldt |
|---|---|---|---|
| 1,585,934 | A | 12/1923 | Muir |
| 1,663,761 | A | 2/1927 | Johnson |
| 2,953,934 | A | 9/1960 | Sundt |
| 3,019,733 | A | 2/1962 | Braid |
| 3,224,434 | A | 12/1965 | Molomut et al. |
| 3,477,423 | A | 11/1969 | Griffith |
| 3,512,519 | A | 5/1970 | Hall |
| 3,561,429 | A | 2/1971 | Jewett et al. |
| 3,565,074 | A | 2/1971 | Foti |
| 3,606,878 | A | 9/1971 | Kellogg |
| 3,727,602 | A | 4/1973 | Hayden et al. |
| 3,732,825 | A | 5/1973 | Apotheloz |
| 3,732,858 | A | 5/1973 | Banko |
| 3,800,783 | A | 4/1974 | Jamshidi |
| 3,844,272 | A | 10/1974 | Banko |

(Continued)

FOREIGN PATENT DOCUMENTS

| DE | 2848314 | 10/1979 |
|---|---|---|
| DE | 3924291 | 1/1991 |

(Continued)

OTHER PUBLICATIONS

International Search Report and Written Opinion dated Sep. 17, 2018 for PCT/US2018/033235.

(Continued)

*Primary Examiner* — Sean P Dougherty

(74) *Attorney, Agent, or Firm* — Dorsey & Whitney LLP

(57) ABSTRACT

A biopsy needle device is disclosed. The biopsy needle device may be configured to be advanced to a predetermined tissue sample, sever the tissue sample, and extract the tissue sample from a body tissue of a patient. The biopsy needle device may be further configured to dislodge the tissue sample from the biopsy needle device utilizing a stylet.

20 Claims, 13 Drawing Sheets

(56) References Cited

U.S. PATENT DOCUMENTS

| | | | |
|---|---|---|---|
| 3,882,849 A | 5/1975 | Jamshidi | |
| 4,275,730 A | 6/1981 | Hussein | |
| 4,282,884 A | 8/1981 | Boebel | |
| 4,306,570 A | 12/1981 | Matthews | |
| 4,354,092 A | 10/1982 | Manabe et al. | |
| 4,416,305 A | 11/1983 | Commette et al. | |
| 4,445,509 A | 5/1984 | Auth | |
| 4,490,137 A | 12/1984 | Moukheibir | |
| 4,549,554 A | 10/1985 | Markham | |
| 4,557,265 A | 12/1985 | Anderson | |
| 4,577,629 A | 3/1986 | Martinez | |
| 4,589,414 A | 5/1986 | Yoshida et al. | |
| 4,598,710 A | 7/1986 | Kleinberg et al. | |
| 4,603,694 A | 8/1986 | Wheeler | |
| 4,605,011 A | 8/1986 | Naslund | |
| 4,617,430 A | 10/1986 | Bryant | |
| 4,620,539 A | 11/1986 | Andrews et al. | |
| 4,643,197 A | 2/1987 | Greene et al. | |
| 4,645,153 A | 2/1987 | Granzow et al. | |
| 4,662,869 A | 5/1987 | Wright | |
| 4,678,459 A | 7/1987 | Onik et al. | |
| 4,683,885 A | 8/1987 | Hutterer et al. | |
| 4,696,298 A | 9/1987 | Higgins et al. | |
| 4,702,260 A | 10/1987 | Wang | |
| 4,708,147 A | 11/1987 | Haaga | |
| 4,776,346 A | 10/1988 | Beraha et al. | |
| 4,844,087 A | 7/1989 | Garg | |
| 4,850,354 A | 7/1989 | McGurk-Burleson et al. | |
| 4,893,635 A | 1/1990 | de Groot et al. | |
| 4,907,598 A | 3/1990 | Bauer | |
| RE33,258 E | 7/1990 | Onik et al. | |
| 4,940,061 A | 7/1990 | Terwilliger et al. | |
| 4,944,308 A * | 7/1990 | Åkerfeldt | A61B 10/0275 |
| | | | 600/564 |
| 4,952,817 A | 8/1990 | Bolan et al. | |
| 4,958,625 A | 9/1990 | Bates et al. | |
| 4,967,762 A | 11/1990 | Devries | |
| 4,986,278 A | 1/1991 | Ravid et al. | |
| 4,986,279 A | 1/1991 | O'Neill | |
| 4,986,807 A | 1/1991 | Farr | |
| 4,989,614 A | 2/1991 | Dejter, Jr. et al. | |
| 5,025,797 A | 6/1991 | Baran | |
| 5,125,413 A | 6/1992 | Baran | |
| 5,138,245 A | 8/1992 | Mattinger et al. | |
| 5,146,921 A | 9/1992 | Terwilliger et al. | |
| 5,158,528 A | 10/1992 | Walker et al. | |
| 5,176,628 A | 1/1993 | Charles et al. | |
| 5,225,763 A | 7/1993 | Krohn et al. | |
| 5,226,910 A | 7/1993 | Kajiyama et al. | |
| 5,234,000 A | 8/1993 | Hakky et al. | |
| 5,236,334 A | 8/1993 | Bennett | |
| 5,249,583 A | 10/1993 | Mallaby | |
| 5,269,791 A | 12/1993 | Mayzels et al. | |
| 5,282,476 A | 2/1994 | Terwilliger | |
| 5,282,477 A | 2/1994 | Bauer | |
| 5,284,472 A | 2/1994 | Sussman et al. | |
| 5,292,327 A | 3/1994 | Dodd et al. | |
| 5,306,260 A * | 4/1994 | Kanner | A61B 17/3403 |
| | | | 604/263 |
| 5,320,110 A * | 6/1994 | Wang | A61B 10/0275 |
| | | | 600/566 |
| 5,324,306 A | 6/1994 | Makower et al. | |
| 5,334,183 A | 8/1994 | Wuchinich | |
| 5,336,229 A | 8/1994 | Noda | |
| 5,361,504 A | 11/1994 | Huang | |
| 5,368,029 A | 11/1994 | Holcombe et al. | |
| 5,368,045 A | 11/1994 | Clement et al. | |
| 5,395,313 A | 3/1995 | Naves et al. | |
| 5,400,798 A | 3/1995 | Baran | |
| 5,409,013 A | 4/1995 | Clement | |
| 5,439,474 A | 8/1995 | Li | |
| 5,441,510 A | 8/1995 | Simpson et al. | |
| 5,449,001 A * | 9/1995 | Terwilliger | A61B 10/0275 |
| | | | 600/567 |
| 5,458,112 A | 10/1995 | Weaver | |
| 5,469,860 A | 11/1995 | De Santis | |
| 5,479,486 A | 12/1995 | Saji | |
| 5,485,917 A | 1/1996 | Early | |
| 5,492,130 A | 2/1996 | Chiou | |
| 5,505,210 A | 4/1996 | Clement | |
| 5,511,556 A | 4/1996 | De Santis | |
| 5,526,822 A | 6/1996 | Burbank et al. | |
| 5,527,322 A | 6/1996 | Clement | |
| 5,535,755 A | 7/1996 | Heske | |
| 5,546,957 A | 8/1996 | Heske | |
| 5,554,151 A | 9/1996 | Hinchliffe | |
| 5,560,373 A | 10/1996 | De Santis | |
| 5,562,685 A | 10/1996 | Mollenauer et al. | |
| 5,564,436 A | 10/1996 | Hakky et al. | |
| 5,569,277 A | 10/1996 | Evans et al. | |
| 5,569,284 A | 10/1996 | Young et al. | |
| 5,575,293 A | 11/1996 | Miller et al. | |
| 5,582,616 A | 12/1996 | Bolduc et al. | |
| 5,591,170 A | 1/1997 | Speivack et al. | |
| 5,601,585 A | 2/1997 | Banik et al. | |
| 5,602,449 A | 2/1997 | Krause et al. | |
| 5,617,874 A | 4/1997 | Baran | |
| 5,643,304 A | 7/1997 | Schechter et al. | |
| 5,649,547 A | 7/1997 | Ritchart et al. | |
| 5,655,542 A | 8/1997 | Weilandt | |
| 5,655,657 A | 8/1997 | Roshdy | |
| 5,665,101 A | 9/1997 | Becker et al. | |
| 5,669,394 A | 9/1997 | Bergey | |
| 5,699,909 A | 12/1997 | Foster | |
| 5,700,265 A | 12/1997 | Romano | |
| 5,709,697 A | 1/1998 | Ratcliff et al. | |
| 5,720,760 A | 2/1998 | Becker et al. | |
| 5,735,264 A | 4/1998 | Siczek et al. | |
| 5,752,923 A | 5/1998 | Terwilliger | |
| 5,755,714 A | 5/1998 | Murphy-Chutorian | |
| 5,766,135 A | 6/1998 | Terwilliger | |
| 5,769,086 A | 6/1998 | Ritchart et al. | |
| 5,769,795 A | 6/1998 | Terwilliger | |
| 5,775,333 A * | 7/1998 | Burbank | A61B 10/0266 |
| | | | 600/567 |
| 5,788,651 A | 8/1998 | Weilandt | |
| 5,792,167 A | 8/1998 | Kablik et al. | |
| 5,807,282 A | 9/1998 | Fowler | |
| 5,817,033 A | 10/1998 | De Santis et al. | |
| 5,817,034 A | 10/1998 | Milliman et al. | |
| 5,823,970 A | 10/1998 | Terwilliger | |
| 5,827,305 A | 10/1998 | Gordon | |
| 5,830,219 A | 11/1998 | Bird et al. | |
| D403,405 S | 12/1998 | Terwilliger | |
| 5,857,982 A | 1/1999 | Milliman et al. | |
| 5,879,365 A | 3/1999 | Whitfield et al. | |
| 5,908,233 A | 6/1999 | Heskett et al. | |
| 5,913,857 A | 6/1999 | Ritchart et al. | |
| 5,916,198 A | 6/1999 | Dillow | |
| 5,916,229 A | 6/1999 | Evans | |
| 5,928,164 A | 7/1999 | Burbank et al. | |
| 5,944,673 A | 8/1999 | Gregoire et al. | |
| 5,951,490 A | 9/1999 | Fowler | |
| 5,951,575 A | 9/1999 | Bolduc et al. | |
| 5,964,716 A | 10/1999 | Gregoire et al. | |
| 5,971,939 A | 10/1999 | De Santis et al. | |
| 5,976,164 A | 11/1999 | Bencini et al. | |
| 5,980,469 A | 11/1999 | Burbank et al. | |
| 5,980,545 A | 11/1999 | Pacala et al. | |
| 6,007,495 A | 12/1999 | Matula | |
| 6,007,497 A | 12/1999 | Huitema | |
| 6,007,556 A | 12/1999 | Kablik et al. | |
| 6,017,316 A | 1/2000 | Ritchart et al. | |
| 6,018,227 A | 1/2000 | Kumar et al. | |
| 6,019,733 A | 2/2000 | Farascioni | |
| 6,022,324 A | 2/2000 | Skinner | |
| 6,022,325 A | 2/2000 | Siczek et al. | |
| 6,027,458 A | 2/2000 | Janssens | |
| 6,036,657 A | 3/2000 | Milliman et al. | |
| 6,050,955 A | 4/2000 | Bryan et al. | |
| 6,077,230 A | 6/2000 | Gregoire et al. | |
| 6,083,176 A | 7/2000 | Terwilliger | |
| 6,083,237 A | 7/2000 | Huitema et al. | |
| 6,086,544 A | 7/2000 | Hibner et al. | |

(56) References Cited

U.S. PATENT DOCUMENTS

| | | | |
|---|---|---|---|
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,361,504 B1 | 3/2002 | Shin |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,436,054 B1 | 8/2002 | Viola et al. |
| 6,482,158 B2 | 11/2002 | Mault |
| 6,485,436 B1 | 11/2002 | Truckai et al. |
| 6,488,636 B2 | 12/2002 | Bryan et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,551,255 B2 | 4/2003 | Van Bladel et al. |
| 6,554,779 B2 | 4/2003 | Viola et al. |
| 6,585,664 B2 | 7/2003 | Burdoff et al. |
| 6,585,694 B1 | 7/2003 | Smith et al. |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Horner et al. |
| 7,025,732 B2 | 4/2006 | Thompson et al. |
| 7,048,694 B2 | 5/2006 | Mark et al. |
| D525,583 S | 7/2006 | Vu |
| 7,153,274 B2 | 12/2006 | Stephens et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,276,032 B2 | 10/2007 | Hibner et al. |
| 7,328,794 B2 | 2/2008 | Lubs et al. |
| 7,347,829 B2 | 3/2008 | Mark et al. |
| 7,374,544 B2 | 5/2008 | Freeman et al. |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,432,813 B2 | 10/2008 | Postma |
| 7,452,367 B2 | 11/2008 | Rassman et al. |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,762,961 B2 | 7/2010 | Heske et al. |
| 7,828,746 B2 | 11/2010 | Teague |
| 7,854,706 B2 | 12/2010 | Hibner |
| 7,883,476 B2 | 2/2011 | Miller et al. |
| 8,251,917 B2 | 8/2012 | Almazan |
| 9,474,527 B1 | 10/2016 | Knodel et al. |
| 2001/0005778 A1 | 6/2001 | Ouchi |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0045840 A1 | 4/2002 | Voegele et al. |
| 2002/0065474 A1 | 5/2002 | Viola |
| 2002/0067151 A1 | 6/2002 | Tanishita |
| 2002/0068878 A1 | 6/2002 | Jasonni et al. |
| 2002/0077646 A1 | 6/2002 | Truwit et al. |
| 2002/0082518 A1 | 6/2002 | Weiss et al. |
| 2002/0107043 A1 | 8/2002 | Adamson et al. |
| 2002/0120212 A1 | 8/2002 | Ritchart et al. |
| 2002/0151822 A1 | 10/2002 | Brudorff et al. |
| 2002/0156395 A1 | 10/2002 | Stephens et al. |
| 2003/0114875 A1 | 6/2003 | Sjostrom |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0049128 A1 | 3/2004 | Miller et al. |
| 2004/0054299 A1 | 3/2004 | Burdorff et al. |
| 2004/0092992 A1 | 5/2004 | Adams et al. |
| 2004/0133124 A1* | 7/2004 | Bates ............... A61B 10/0275 600/564 |
| 2004/0167427 A1 | 8/2004 | Quick et al. |
| 2004/0186393 A1 | 9/2004 | Leigh et al. |
| 2004/0215103 A1 | 10/2004 | Mueller et al. |
| 2004/0220495 A1 | 11/2004 | Cahir et al. |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0080355 A1 | 4/2005 | Mark |
| 2005/0085838 A1 | 4/2005 | Thompson et al. |
| 2005/0101879 A1 | 5/2005 | Shidham et al. |
| 2005/0113715 A1 | 5/2005 | Scwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |

(56) References Cited

U.S. PATENT DOCUMENTS

| | | |
|---|---|---|
| 2005/0209530 A1 | 9/2005 | Pflueger |
| 2005/0275378 A1 | 12/2005 | Canino et al. |
| 2005/0277829 A1 | 12/2005 | Tsonton et al. |
| 2005/0277871 A1 | 12/2005 | Selis |
| 2006/0030784 A1 | 2/2006 | Miller et al. |
| 2006/0074344 A1 | 4/2006 | Hibner |
| 2006/0074345 A1 | 4/2006 | Hibner |
| 2006/0074346 A1 | 4/2006 | Hibner |
| 2006/0113958 A1 | 6/2006 | Lobert et al. |
| 2006/0116603 A1 | 6/2006 | Shibazaki et al. |
| 2006/0129063 A1 | 6/2006 | Thompson et al. |
| 2006/0173377 A1 | 8/2006 | McCullough et al. |
| 2006/0178666 A1 | 8/2006 | Cosman et al. |
| 2006/0184063 A1 | 8/2006 | Miller |
| 2006/0241515 A1 | 10/2006 | Jones et al. |
| 2006/0258953 A1 | 11/2006 | Lee |
| 2006/0258956 A1 | 11/2006 | Haberstich et al. |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0068990 A1 | 3/2007 | Shelton et al. |
| 2007/0073326 A1 | 3/2007 | Miller et al. |
| 2007/0090788 A1 | 4/2007 | Hansford et al. |
| 2007/0106176 A1* | 5/2007 | Mark ................ A61B 10/0275 |
| | | 606/167 |
| 2007/0118049 A1 | 5/2007 | Viola |
| 2007/0149894 A1 | 6/2007 | Heske et al. |
| 2007/0161925 A1 | 7/2007 | Quick et al. |
| 2007/0167782 A1 | 7/2007 | Callahan et al. |
| 2007/0179401 A1 | 8/2007 | Hibner |
| 2007/0213590 A1 | 9/2007 | Squicciarina |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0293788 A1 | 12/2007 | Entrekin et al. |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0071193 A1 | 3/2008 | Reuber et al. |
| 2008/0079391 A1 | 4/2008 | Schroeck et al. |
| 2008/0110261 A1 | 5/2008 | Randall et al. |
| 2008/0135443 A1 | 6/2008 | Frojd et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson |
| 2008/0183099 A1 | 7/2008 | Jorgensen et al. |
| 2008/0195066 A1 | 8/2008 | Speeg et al. |
| 2008/0200833 A1 | 8/2008 | Jardin et al. |
| 2008/0200836 A1 | 8/2008 | Speeg et al. |
| 2008/0208194 A1 | 8/2008 | Bichenbach |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0223904 A1 | 9/2008 | Marczyk |
| 2008/0228104 A1 | 9/2008 | Uber et al. |
| 2008/0232604 A1 | 9/2008 | Dufresne et al. |
| 2008/0234715 A1 | 9/2008 | Pescue et al. |
| 2008/0281225 A1 | 11/2008 | Spero et al. |
| 2008/0281226 A1* | 11/2008 | Peters ................ A61B 10/0266 |
| | | 600/567 |
| 2008/0287826 A1 | 11/2008 | Videbaek et al. |
| 2008/0306404 A1 | 12/2008 | Ronald |
| 2008/0306406 A1 | 12/2008 | Thompson et al. |
| 2008/0308607 A1 | 12/2008 | Timm et al. |
| 2008/0312554 A1 | 12/2008 | Garrison |
| 2008/0319341 A1 | 12/2008 | Taylor et al. |
| 2009/0030405 A1 | 1/2009 | Quick et al. |
| 2009/0062624 A1 | 3/2009 | Neville |
| 2009/0088666 A1* | 4/2009 | Miller ................ A61B 10/0275 |
| | | 600/568 |
| 2009/0125062 A1 | 5/2009 | Arnin |
| 2009/0137927 A1 | 5/2009 | Miller |
| 2009/0163870 A1* | 6/2009 | Flagle ................ A61B 10/0275 |
| | | 604/164.01 |
| 2009/0171243 A1 | 7/2009 | Hibner et al. |
| 2009/0204021 A1 | 8/2009 | Shabaz et al. |
| 2009/0082695 A1 | 9/2009 | Whitehead |
| 2009/0227893 A1 | 9/2009 | Coonahan et al. |
| 2010/0030020 A1 | 2/2010 | Sanders et al. |
| 2010/0063416 A1 | 3/2010 | Cicenas et al. |
| 2010/0114031 A1* | 5/2010 | Jarial ................ A61B 10/0275 |
| | | 604/164.11 |
| 2010/0152611 A1 | 6/2010 | Parihar et al. |
| 2010/0160820 A1 | 6/2010 | Weikel, Jr. et al. |
| 2010/0210966 A1 | 8/2010 | Videbaek |
| 2010/0234760 A1 | 9/2010 | Almazan |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2011/0071391 A1 | 3/2011 | Speeg |
| 2011/0152715 A1 | 6/2011 | Delap et al. |
| 2011/0160611 A1 | 6/2011 | Ritchart et al. |
| 2011/0224577 A1 | 9/2011 | Park |
| 2011/0237976 A1 | 9/2011 | Weitzel et al. |
| 2011/0313316 A1 | 12/2011 | Ranpura et al. |
| 2012/0022397 A1* | 1/2012 | Jarial ................ A61B 10/0275 |
| | | 600/567 |
| 2012/0116248 A1 | 5/2012 | Mcweeney et al. |
| 2012/0130274 A1 | 5/2012 | Persat |
| 2012/0197157 A1 | 8/2012 | Ryan et al. |
| 2012/0215130 A1 | 8/2012 | Field et al. |
| 2012/0253228 A1 | 10/2012 | Schembre et al. |
| 2013/0046316 A1 | 2/2013 | Sullivan et al. |
| 2013/0131547 A1* | 5/2013 | Hardert ................ A61B 10/0275 |
| | | 600/567 |
| 2014/0100448 A1* | 4/2014 | Neilan ................ A61B 10/0275 |
| | | 600/566 |
| 2014/0207021 A1* | 7/2014 | Snow ................ A61B 10/0275 |
| | | 600/564 |
| 2014/0228705 A1* | 8/2014 | Linderman ........ A61B 10/0283 |
| | | 600/566 |
| 2014/0276205 A1 | 9/2014 | Miller et al. |
| 2014/0296741 A1 | 10/2014 | Austen |
| 2014/0371585 A1 | 12/2014 | Thompson et al. |
| 2015/0119916 A1 | 4/2015 | Dietz et al. |
| 2015/0342580 A1* | 12/2015 | Clancy ................ A61B 17/3417 |
| | | 600/567 |
| 2016/0030016 A1 | 2/2016 | Mcweeney et al. |
| 2016/0081678 A1 | 3/2016 | Kappel et al. |
| 2016/0128784 A1 | 5/2016 | Ahari |
| 2016/0324508 A1 | 11/2016 | Duggan et al. |
| 2016/0354066 A1* | 12/2016 | Asaoka ................ A61B 8/4416 |
| 2018/0333145 A1* | 11/2018 | Snow ................ A61B 10/0275 |
| 2018/0333146 A1 | 11/2018 | Hallisey et al. |
| 2019/0110779 A1 | 4/2019 | Gardner et al. |
| 2021/0093305 A1 | 4/2021 | Peliks et al. |

FOREIGN PATENT DOCUMENTS

| | | |
|---|---|---|
| DE | 4120329 | 1/1992 |
| DE | 4041614 | 10/1992 |
| DE | 2453058 | 5/1996 |
| DE | 10034297 | 4/2001 |

(56) References Cited

FOREIGN PATENT DOCUMENTS

| | | |
|---|---|---|
| DE | 10026303 | 2/2002 |
| DE | 20209525 | 11/2002 |
| DE | 10235480 | 2/2004 |
| EP | 0433717 | 6/1991 |
| EP | 541377 | 5/1993 |
| EP | 0890339 | 1/1999 |
| EP | 0995400 | 4/2000 |
| EP | 1074271 | 2/2001 |
| EP | 1520518 | 4/2005 |
| EP | 1579809 | 9/2005 |
| EP | 1665958 | 6/2006 |
| EP | 2095772 | 2/2009 |
| EP | 2106750 | 10/2009 |
| FR | 1345429 | 12/1963 |
| FR | 2739293 | 4/1997 |
| GB | 2018601 | 10/1979 |
| GB | 2038640 | 12/1979 |
| JP | H10508504 | 8/1998 |
| JP | 2005530554 | 10/2005 |
| JP | 2006509545 | 3/2006 |
| JP | 2006528907 | 12/2006 |
| JP | 2007502159 | 2/2007 |
| RU | 1454457 | 1/1989 |
| WO | 199314700 | 8/1993 |
| WO | 199416181 | 7/1994 |
| WO | 199428801 | 12/1994 |
| WO | 199628097 | 9/1996 |
| WO | 199825522 | 6/1998 |
| WO | 199831285 | 7/1998 |
| WO | 199835615 | 8/1998 |
| WO | 199846290 | 10/1998 |
| WO | 199915079 | 4/1999 |
| WO | 199933501 | 7/1999 |
| WO | 200004832 | 2/2000 |
| WO | 200030546 | 6/2000 |
| WO | 200059378 | 10/2000 |
| WO | 200172230 | 10/2001 |
| WO | 200222023 | 3/2002 |
| WO | 200232318 | 4/2002 |
| WO | 2002069808 | 9/2002 |
| WO | 20040757719 | 9/2004 |
| WO | 2005013830 | 2/2005 |
| WO | 2006015302 | 2/2006 |
| WO | 2007047128 | 4/2007 |
| WO | 2007095330 | 8/2007 |
| WO | 2007112751 | 10/2007 |
| WO | 2008021687 | 2/2008 |
| WO | 2008024684 | 2/2008 |
| WO | 200804812 | 4/2008 |
| WO | 2008131362 | 10/2008 |
| WO | 2010107424 | 9/2010 |
| WO | 2013158072 | 10/2013 |
| WO | 2014081812 | 5/2014 |

OTHER PUBLICATIONS

International Search Report and Written Opinion dated Jul. 2, 2009 for PCT/KR2009/006741.
International Search Report and Written Opinion dated Sep. 4, 2018 for PCT/US2018/033188.
International Search Report and Written Opinion dated Sep. 11, 2018 for PCT/US2018/032789.
Office Action dated Jul. 1, 2020 for U.S. Appl. No. 15/980,116.
Office Action dated May 12, 2020 for U.S. Appl. No. 15/982,624.
European Search Report dated Jan. 26, 2021 for EP18801552.3.
European Search Report dated Feb. 1, 2021 for EP18802126.5.
European Search Report dated Feb. 4, 2021 for EP18801940.0.
Notice of Allowance dated Jul. 9, 2021 for U.S. Appl. No. 15/982,624.
Notice of Allowance dated Aug. 25, 2021 for U.S. Appl. No. 15/965,109.
Office Action dated Aug. 2, 2021 for U.S. Appl. No. 15/980,116.
Office Action dated Jan. 3, 2023 for U.S. Appl. No. 15/980,116.
Office Action dated Aug. 29, 2022 for U.S. Appl. No. 15/980,116.
Office Action dated Feb. 28, 2022 for U.S. Appl. No. 15/980,116.
Office Action dated Nov. 17, 2020 for U.S. Appl. No. 15/982,624.
European Search Report dated May 7, 2021 for EP18801940.0.
Office Action dated Mar. 24, 2021 for U.S. Appl. No. 15/980,116.

\* cited by examiner

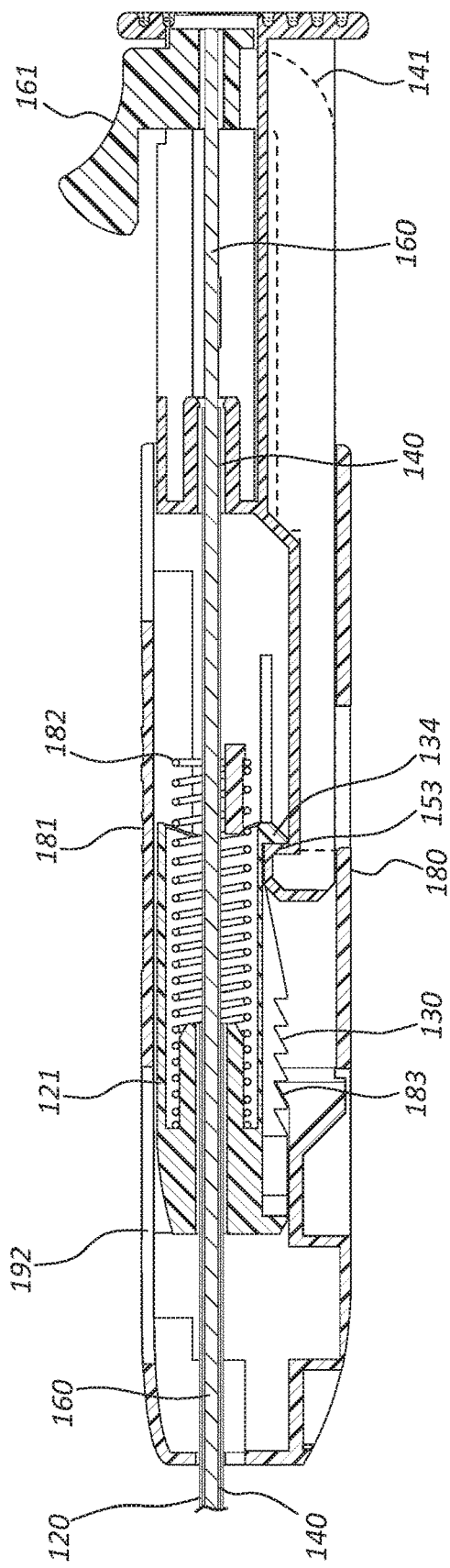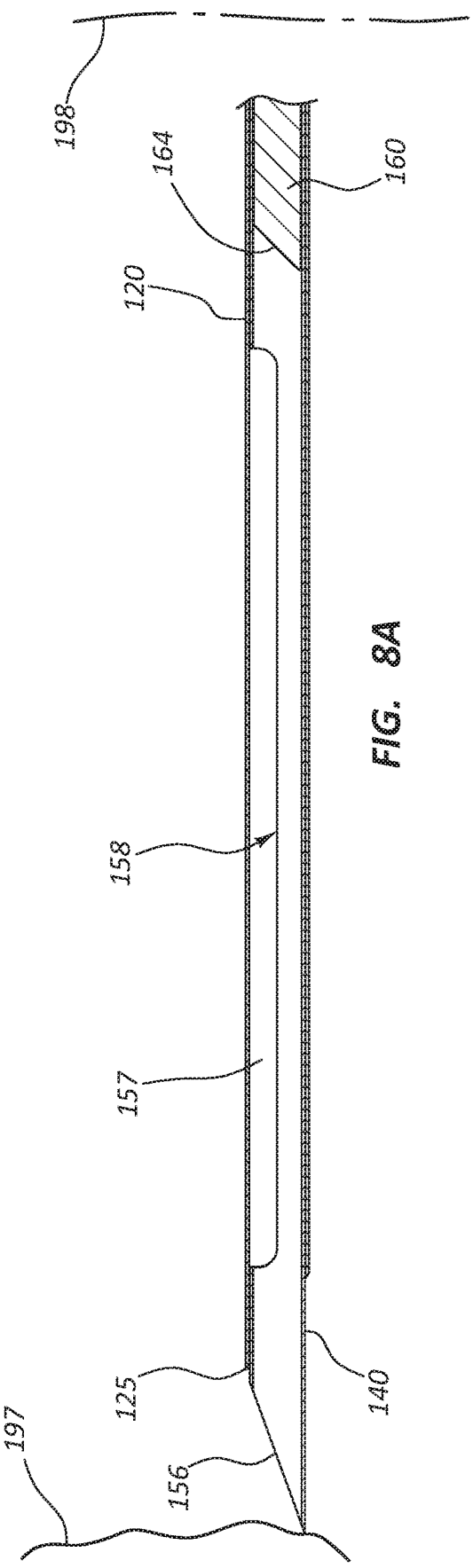
FIG. 8
FIG. 8A

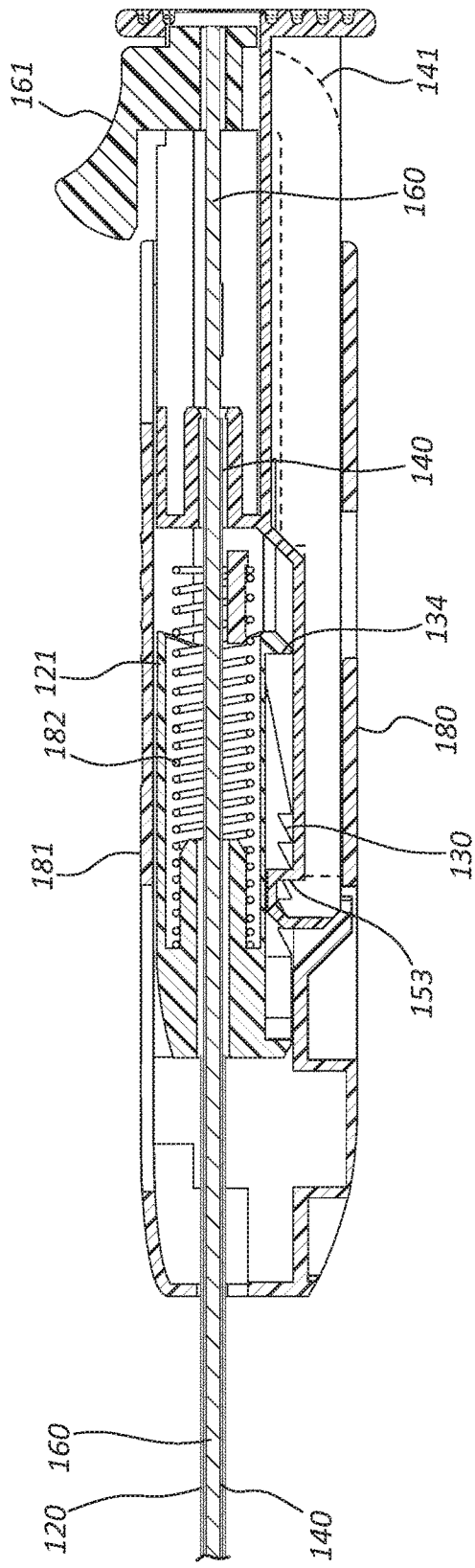
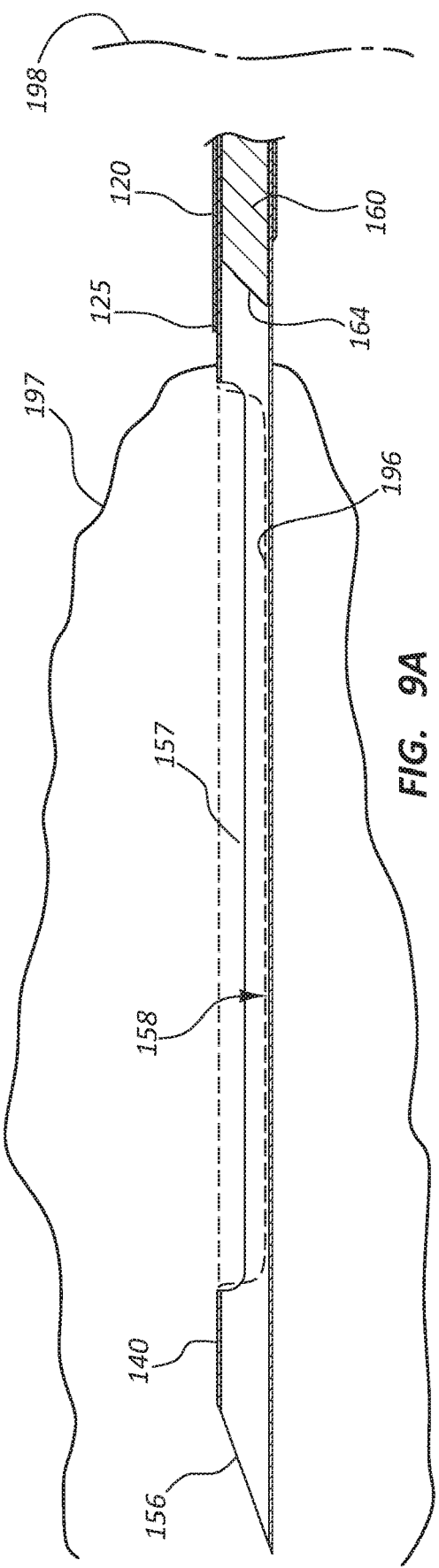
FIG. 9
FIG. 9A

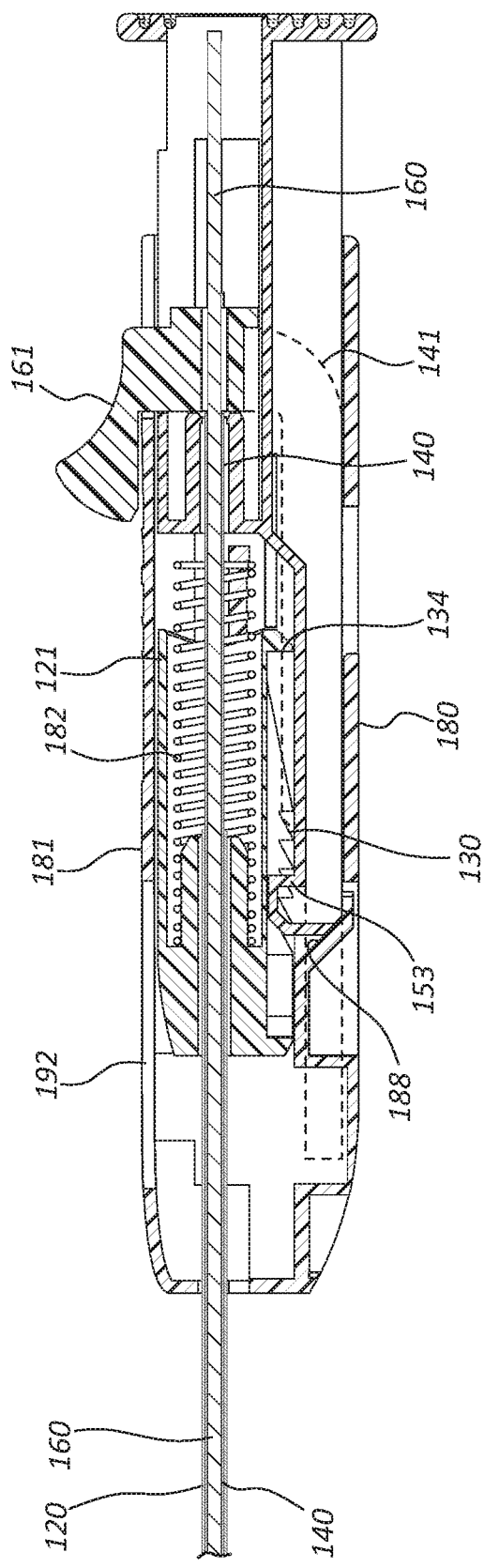
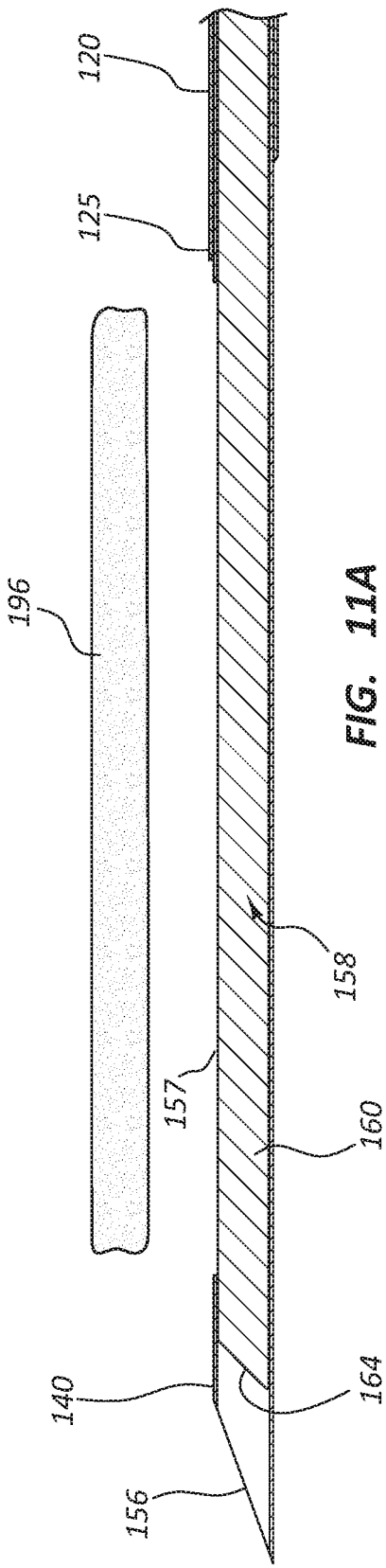
FIG. 11
FIG. 11A

BIOPSY NEEDLE DEVICES AND METHODS OF USE

RELATED APPLICATIONS

This application claims priority to U.S. Provisional Application No. 62/508,797, filed on May 19, 2017 and titled, "Biopsy Needle Devices and Methods of Use," which is hereby incorporated by reference in its entirety.

TECHNICAL FIELD

The present disclosure relates generally to medical devices. More specifically, the present disclosure relates to biopsy needle assemblies configured for use with tissue biopsy devices, including needle assemblies configured to decrease, minimize, or eliminate axial translation impact at a tissue sample collection site.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

FIG. 3A is a detail view of a distal end portion of the cannula of FIG. 3 taken through line 3A.

FIG. 4A is a detail view of a distal end portion of the trocar of FIG. 4 taken through line 4A.

FIG. 5A is a detail view of a distal end portion of the stylet of FIG. 5 taken through line 5A.

FIG. 8 is a schematic cross-sectional representation of portions of the biopsy needle device of FIGS. 1 and 2 in a second configuration.

FIG. 8A is a schematic cross-sectional representation of portions of the cannula, the trocar and the stylet of the biopsy needle device of FIG. 8 in the second configuration shown in FIG. 8.

FIG. 9 is a schematic cross-sectional representation of portions of the biopsy needle device of FIGS. 1 and 2 in a third configuration.

FIG. 9A is a schematic cross-sectional representation of portions of the cannula, the trocar and the stylet of the biopsy needle device of FIG. 9 in the third configuration shown in FIG. 9.

FIG. 11 is a schematic cross-sectional representation of portions of the biopsy needle device of FIGS. 1 and 2 in a fifth configuration.

FIG. 11A is a schematic cross-sectional representation of portions of the cannula, the trocar and the stylet of the biopsy needle device of FIG. 11 in the fifth configuration shown in FIG. 11.

DETAILED DESCRIPTION

Figure 1:
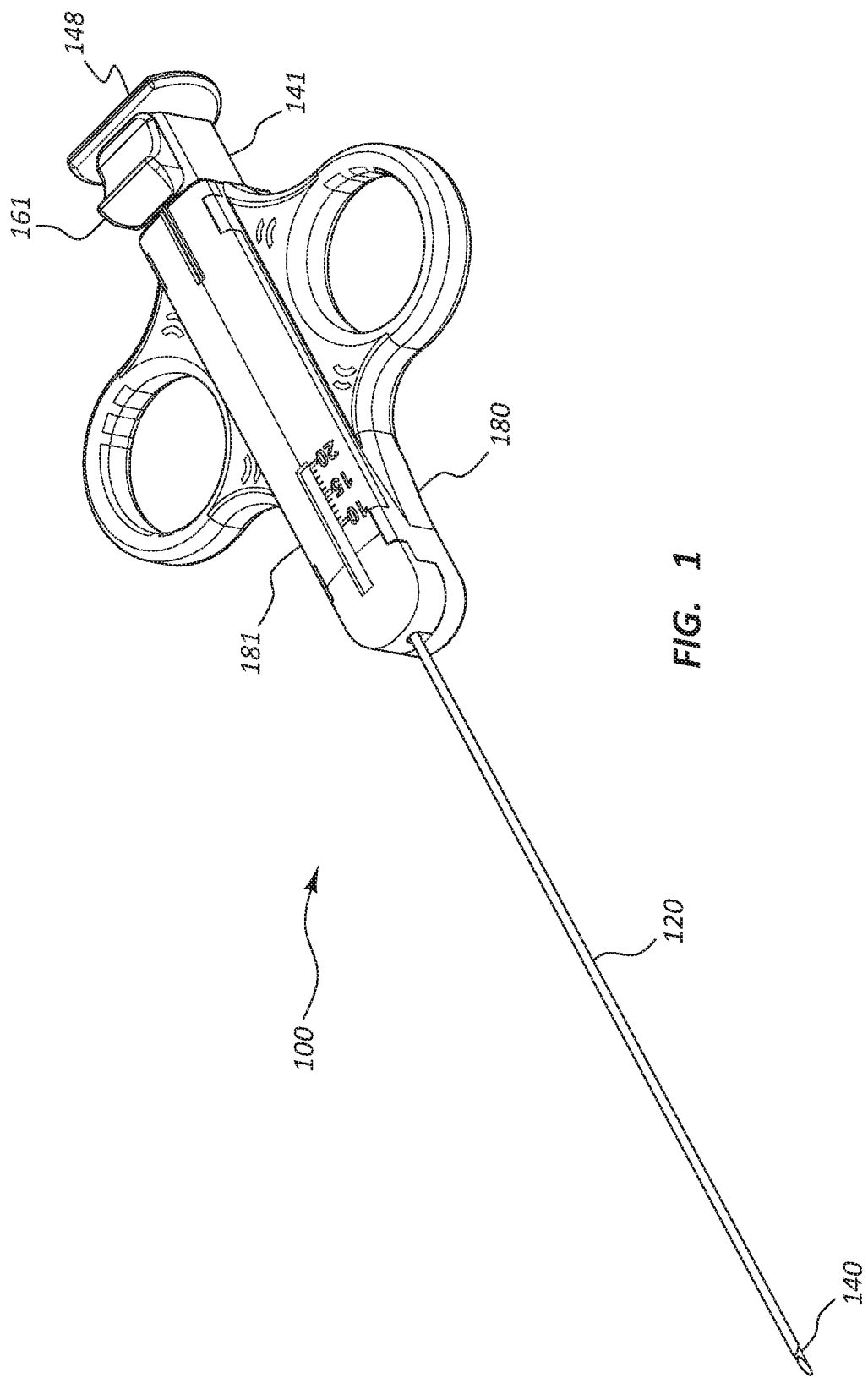
FIG. 1 is a perspective view of a biopsy needle device.

Tissue biopsy devices may be configured to retrieve tissue samples from various locations within a patient's body. For example, a biopsy device may comprise a biopsy needle device, or needle assembly, including tubular members, needles, trocars, cutting styli, styli, cannula, and/or other components configured to access and sever a tissue sample in a medical procedure commonly referred to as Core Needle Biopsy. The biopsy needle device may be advanced to a location within the body through the skin of the patient (percutaneous access), through an open incision or through a body lumen or other structure. A portion of the biopsy needle device may be advanced into a lesion or target tissue. Another portion of the biopsy needle device may then be advanced into the lesion or target tissue to sever a tissue sample from the lesion or target tissue. The biopsy needle device may then be withdrawn from the patient and the tissue sample extracted from the needle assembly for analysis. Furthermore, a biopsy needle device may comprise a handle or actuator configured to axially displace or deflect at least a portion of the biopsy needle device such that the biopsy needle device cuts or severs the targeted tissue sample.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. For example, as specifically applied to the needle portion of the biopsy needle device, the proximal end of the needle refers to the end nearest the handle or actuator and the distal end refers to the opposite end, the end that may be inserted into a patient.

"Tissue" is used in its broadest sense, to refer to any tissue or substance within a human body.

FIGS. 1-11A illustrate different views of a biopsy needle device and related components. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

Figure 2:
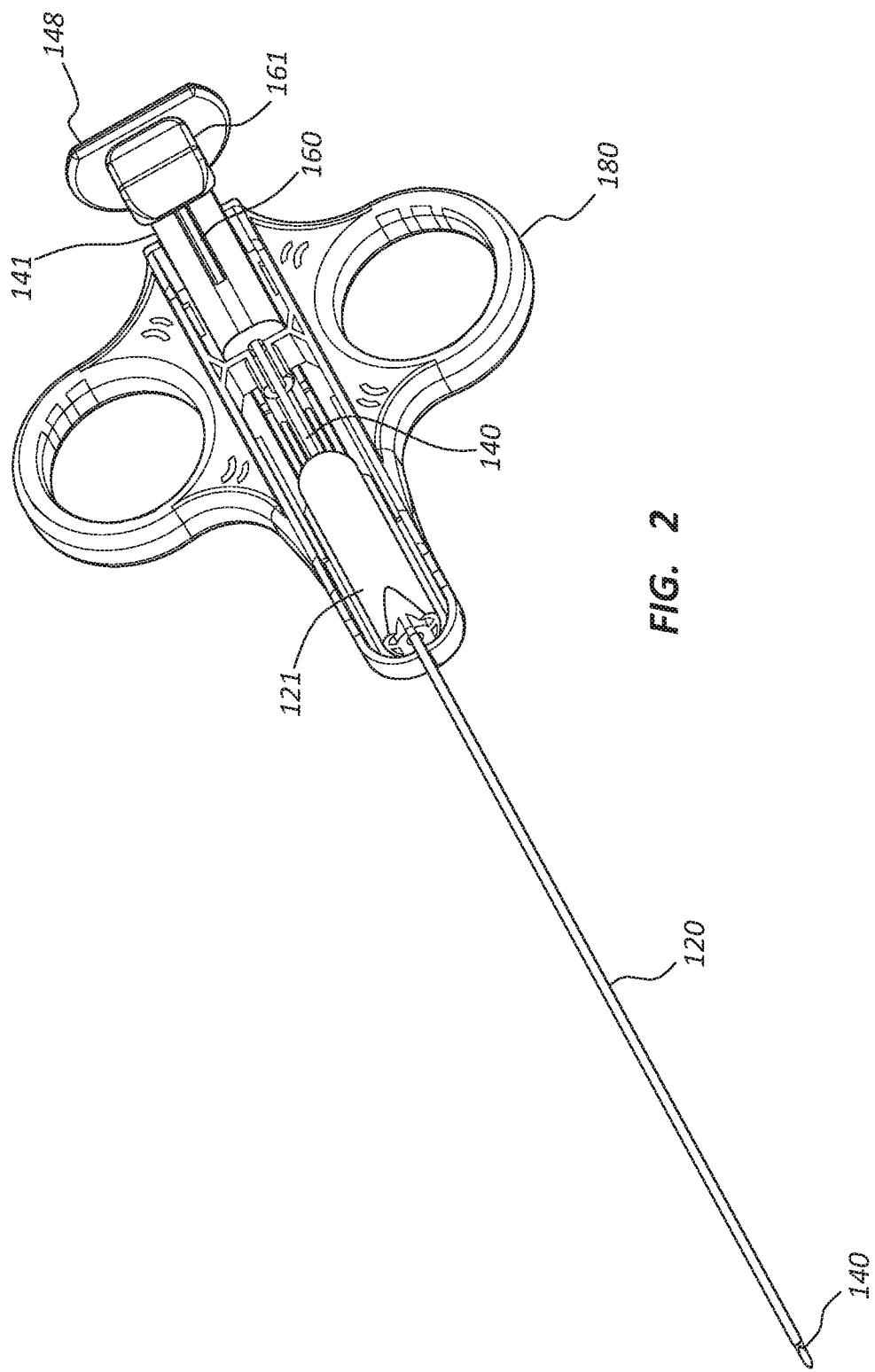
FIG. 2 is a cross-sectional view of the biopsy needle device of FIG. 1 with the housing lid removed.

FIGS. 1 and 2 are perspective views of a biopsy needle device 100. As illustrated, the biopsy needle device 100 may comprise a cannula assembly 102, a trocar assembly 104, a stylet assembly 106 and an actuator 108. The cannula assembly 102 may comprise a cannula 120 and a cannula hub 121. The trocar assembly 104 may comprise a trocar 140 and a trocar hub 141. The stylet assembly 106 may comprise a stylet 160 and a stylet hub 161. The actuator 108 may comprise a housing base 180 and housing lid 181.

Figure 3:
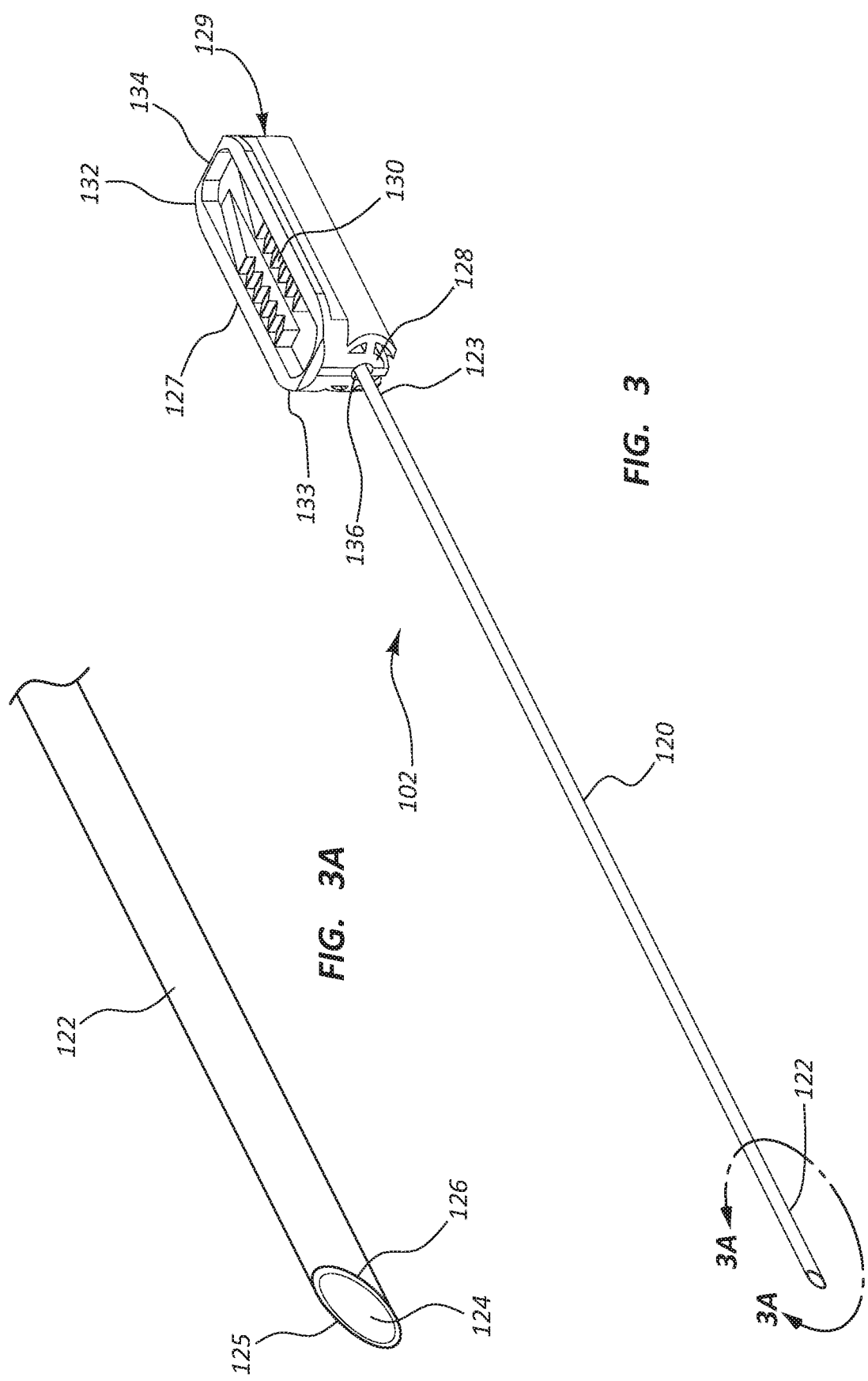
FIG. 3 is a perspective view of a cannula of the biopsy needle device of FIGS. 1 and 2.

FIG. 3 is a perspective view of the cannula assembly 102 of FIGS. 1 and 2, and FIG. 3A is a detail view of a distal end portion 122 of the cannula 120 of FIG. 3. Referring now to FIGS. 3 and 3A, in some embodiments the cannula assembly 102 may comprise the cannula 120 and the cannula hub 121. The cannula 120 may comprise an elongate tube having the distal end portion 122 and a proximal end portion 123. The cannula 120 may range in diameter from 8 gauge to 22 gauge and including from 14 gauge to 20 gauge. A lumen 124 of the cannula 120 may be sized to accommodate the positioning of the trocar 140 within the lumen 124. The length of the cannula 120 may range from 100 cm to 5 cm and including from 25 cm to 10 cm. The cannula 120 may be preferably manufactured from a medical grade stainless steel material.

In some embodiments the proximal end portion 123 of the cannula 120 may be configured to be fixedly coupled to the cannula hub 121 such that the proximal end of the lumen 124 is open to allow for passage of the trocar 140 into the lumen 124. The cannula 120 may be fixedly coupled to the cannula hub 121 using techniques known in the art such as bonding, welding, overmolding, etc. The outside surface of the proximal end portion 123 of the cannula 120 may be modified to enhance the coupling of the cannula 120 to the cannula hub 121. For example, the surface may be chemically or mechanically etched or textured to roughen the surface in order to enhance the adhesion of an adhesive or plastic. Alternatively, the surface may be chemically modified to enhance the adhesion of the adhesive or plastic.

The distal end portion 122 of the cannula 120 may comprise a bevel 125. The bevel 125 may be configured to cut or sever tissue as the cannula 120 slides along the longitudinal axis of the trocar 140. The bevel 125 may have an angle of from 180 degrees to 5 degrees and including from 30 degrees to 25 degrees. Bevel edges 126 may be sharp and may be configured to cut or sever tissue.

In certain embodiments the cannula 120 may comprise a plurality of indicia 135 configured to indicate to the practitioner a distance that the cannula 120 and trocar 140 have advanced into a body tissue (for clarity not all indicia 135 are labeled). For example, each indicium 135 may be positioned 1 cm apart; thus, if the practitioner displaces the cannula 120 and the trocar 140 into a body tissue up to the third indicia 135 from the distal end portion 142 of the trocar 140, it may indicate to the practitioner that approximately 3 cm of the trocar 140 and cannula 120 has been displaced into the body tissue. In some embodiments, the indicia 135 may comprise a plurality of substantially evenly spaced annular lines, marks, or grooves on an outside surface of the cannula 120. In certain embodiments, the indicia 135 may comprise a plurality of tick marks or the indicia 135 may not be evenly spaced.

In certain embodiments, a portion or portions of at least one of the components of the biopsy needle device 100, including, but not limited to, the cannula 120, the trocar 140, and/or the stylet 160, may comprise a radiopaque material and/or an echogenic material. A radiopaque material (for example, in combination with computed tomography or x-ray) may aid the practitioner in directing or displacing the biopsy needle device 100 to a desired or predetermined position within the body tissue of the patient. Bismuth, gold, or other radiopaque materials alone, or in combination, may be used. An echogenic material or surface (for example, in combination with ultrasound) may analogously aid the practitioner in directing or displacing the trocar assembly 104 to a desired or predetermined position within the body tissue of the patient. Surface disruptions such as texturing, grooves, dimples, or a combination of materials may also be used.

The cannula hub 121 may comprise a body 127, a cannula coupling portion 128, a cavity 129 and locking teeth 130. The cannula hub 121 may be disposed within the distal end portion of the housing base 180 and be configured to move along a longitudinal axis of the housing base 180. A cannula coupling portion 128 may be generally cylindrical with a bore 136 having a diameter to accommodate the cannula 120 and a length to provide a secure attachment of the cannula 120 to the cannula coupling portion 128. The cannula coupling portion 128 may be positioned near a distal end 133 of the body 127 of the cannula hub 121. The cavity 129 may extend from the distal end 133 of the body 127 to a proximal end 132 of the body 127. The cavity 129 may be sized to accommodate a spring 182 configured to move the cannula assembly 102 from a proximal configuration to a distal configuration. The locking features, such as teeth 130 of the cannula hub 121, are configured to engage with opposing locking teeth 183 of the housing base 180. The engaging locking teeth 130, 183 may allow for the actuator 108 to be cocked and the cannula assembly 102 to be locked in a selected proximal position. The cannula hub 121 may further comprise a shoulder 134 near the proximal end 132 of the body 127. The shoulder 134 may be configured to engage with a hook member 153 of the trocar hub 141 to allow for cocking of the actuator 108 and selective positioning of the cannula assembly 102 in a proximal position. The cannula hub 121 may be formed from an opaque or translucent plastic material using manufacturing techniques known to the industry such as injection molding, casting, machining, etc.

Figure 4:
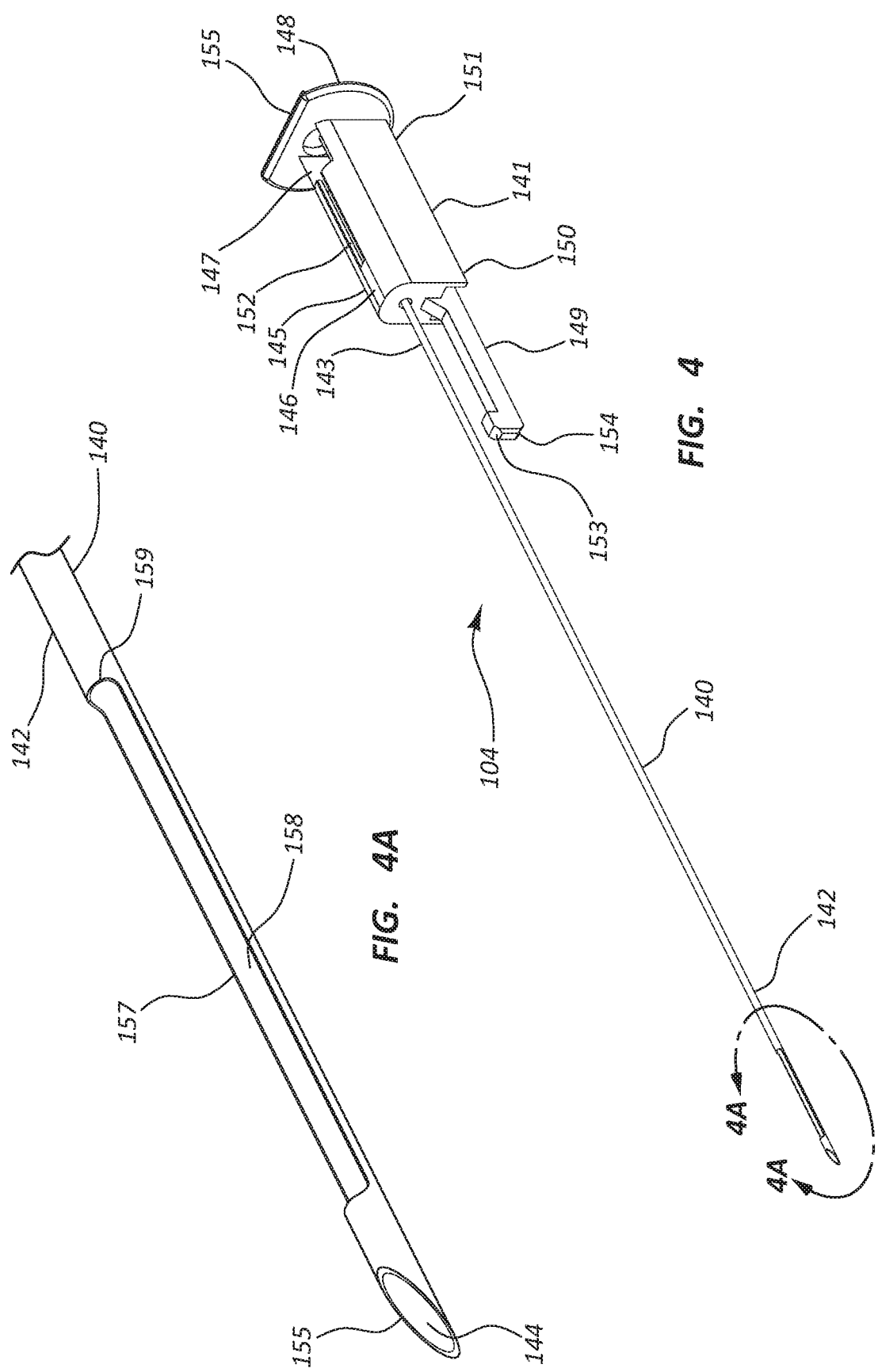
FIG. 4 is a perspective view of a trocar of the biopsy needle device of FIGS. 1 and 2.

FIG. 4 is a perspective view of the trocar assembly 104 of FIGS. 1 and 2, and FIG. 4A is a detail view of a distal end portion 142 of the trocar 140 of FIG. 4 taken from detail line 4A. Referring to FIGS. 4-4A, in some embodiments the trocar assembly 104 may comprise the trocar 140 and the trocar hub 141. The trocar 140 may comprise an elongate tube having the distal end portion 142 and a proximal end portion 143. The trocar 140 may range in diameters and lengths to match the cannula for optimized tissue cutting. The trocar 140 diameter may be configured such that the trocar 140 may be slidingly disposed within the lumen 124 of the cannula 120. The lumen 144 of the trocar 140 may be configured to accommodate the positioning of the stylet 160 within the lumen 144. The trocar 140 may be preferably manufactured from a medical grade stainless steel material.

The distal end portion 142 of the trocar 140 may comprise a bevel 156 and a notch 157. The bevel 156 may be configured to penetrate tissue as the trocar 140 may be inserted into the patient's tissue. The bevel 156 may be configured as any type of tissue penetrating bevel utilized in medical devices comprising a trocar. For example, the bevel 156 type may be a Tri-cut, Whitacre, pencil point, Seldinger, Sprotte, etc.

In some embodiments the notch 157 may be located proximal of the bevel 156. The notch 157 may have a length that is longer than a width. The length of the notch 157 may range from 5 cm to 35 cm and including embodiments where it is about 20 cm. The width of the notch 157 may be approximately equivalent to the outer diameter of the trocar 140. The depth of the notch 157 may be approximately one half of the outer diameter of the trocar 140. The notch 157 may be positioned proximal of the bevel 156. The notch 157 may comprise an open channel 158 having a semi-circular wall. The channel 158 may be configured to capture and retain the tissue sample cut or severed by the cannula (120 of FIG. 3). For example, the trocar 140 may be inserted into the target tissue or lesion. A portion of the target tissue or lesion may collapse into the channel 158. The cannula 120 may then be advanced over the trocar 140 cutting or severing the portion of the target tissue or the lesion from the surrounding tissue. The cut or severed tissue sample may be captured and retained within the channel 158.

In some embodiments the proximal end portion 143 of the trocar 140 may be configured to be fixedly coupled to the trocar hub 141 such that the proximal end of the lumen 144 is open to allow for passage of the stylet 160 into the lumen 144. The trocar 140 may be fixedly coupled to the trocar hub 141 using techniques known in the art such as bonding, welding, overmolding, etc. The outside surface of the proximal end portion 143 of the trocar 140 may be modified to enhance the coupling of the trocar 140 to the trocar hub 141. For example, the surface may be chemically or mechanically etched or textured to roughen the surface in order to enhance the adhesion of an adhesive or plastic. Alternatively, the surface may be chemically modified to enhance the adhesion of the adhesive or plastic.

In some embodiments the trocar hub 141 may comprise a body 145, a trocar coupling portion 146, a cavity 147, an actuation pad 148 and an actuation extension 149. The trocar hub 141 may be disposed within the proximal end portion of the housing base 180 and be configured to move along a longitudinal axis of the housing base 180. The trocar coupling portion 146 may be generally cylindrical with a diameter to accommodate the trocar 140 and a length to provide a secure coupling of the trocar 140 to the trocar coupling portion 146. The trocar coupling portion 146 may be positioned near a distal end 150 of the body 145 of the trocar hub 141. The cavity 147 may extend from the distal end 150 of the body 145 to a proximal end 151 of the body 145. The cavity 147 may be configured to accommodate a portion of the stylet hub 161. The body 145 may further comprise a longitudinal slot 152 configured to allow for distal and proximal movement of the stylet hub 161. The actuation extension 149 of the trocar hub 141 may extend distally from the body 145 of the trocar hub 141. The actuation extension 149 may comprise a hook member 153 at a distal end 154. The hook member 153 may be configured to engage the shoulder 134 of the cannula hub 121 such that proximal movement of the trocar assembly 104 may result in proximal movement of the cannula assembly 102. Additionally, the hook member 153 may be configured to engage with the cannula hub 121 such that the locking teeth 130 of cannula hub 121 may be disengaged from the locking teeth 183 of the housing base 180 allowing for the cannula assembly 102 to move distally. The actuation pad 148 may be located at the proximal end 151 of the body 145. The actuation pad 148 may be configured for placement of the practitioner's thumb or finger when activating the actuator 108. The actuation pad 148 may be configured to accommodate the practitioner's thumb or finger and may comprise a distally facing surface 155 configured to provide a non-slip surface. The surface 155 may comprise, but not limited to, ridges, grooves, detents and/or a textured surface. The trocar hub 141 may be formed from an opaque or translucent plastic material using manufacturing techniques known to the industry such as injection molding, casting, machining, etc.

Figure 5:
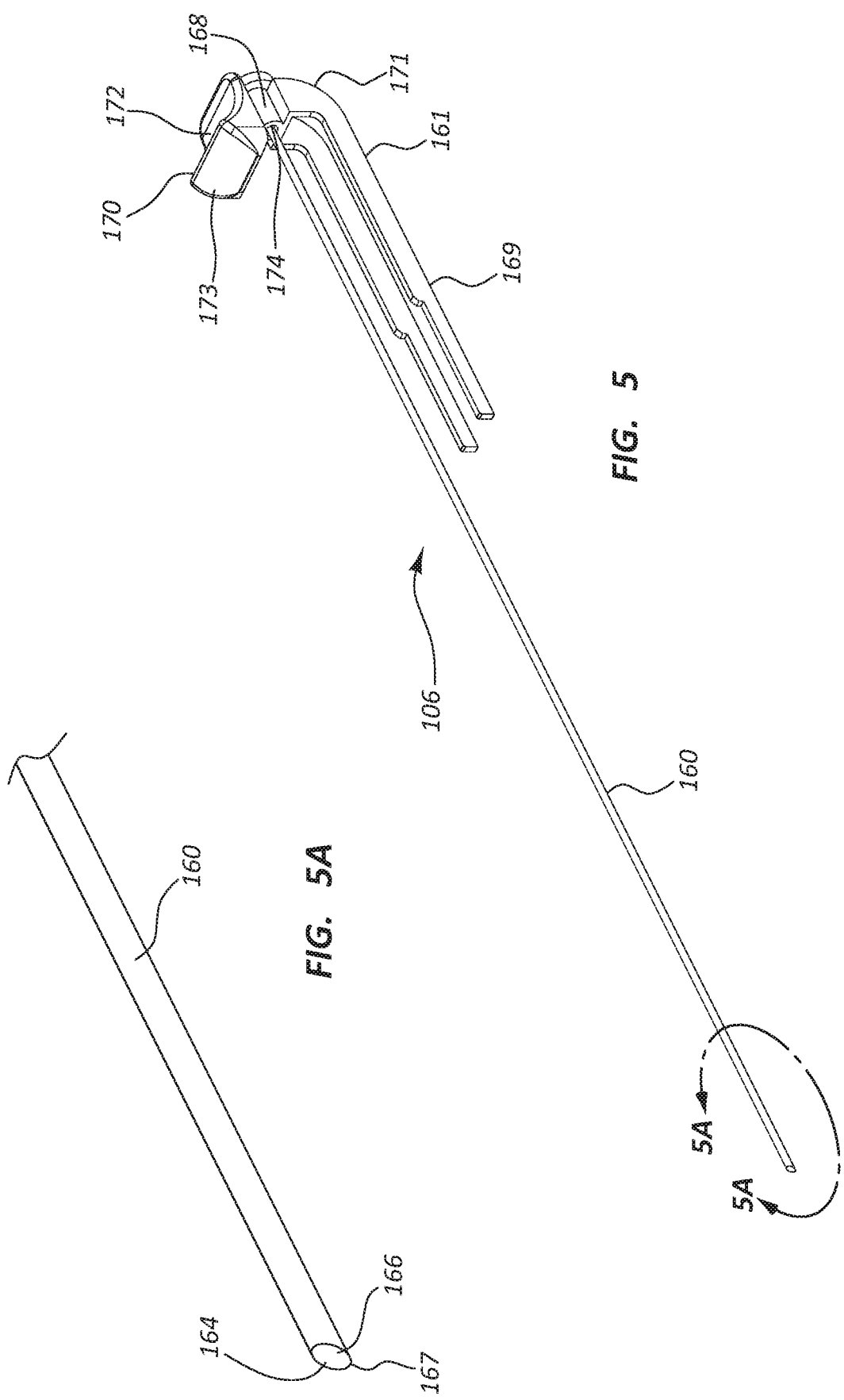
FIG. 5 is a perspective view of a stylet of the biopsy needle device of FIGS. 1 and 2.

FIG. 5 is a perspective view of the stylet assembly 106 of FIGS. 1 and 2, and FIG. 5A is a detail view of a distal end portion 162 of the stylet 160 of FIG. 5 taken from detail line 5A. Referring to FIGS. 5 and 5A, in some embodiments the stylet assembly 106 may comprise the stylet 160 and the stylet hub 161. The stylet 160 may comprise an elongate rod having the distal end portion 162 and a proximal end portion 163. The stylet 160 may range in diameters and lengths to match the cannula and trocar for optimized tissue cutting and sample ejection. The stylet 160 diameter may be sized such that the stylet 160 may be slidingly disposed within the lumen 144 of the trocar 140. The stylet 160 may be preferably manufactured from a medical grade stainless steel material or a rigid plastic material.

The distal end portion 162 of the stylet 160 may comprise a bevel 164. The bevel 164 may be configured to displace the tissue sample from the notch 157 and/or channel 158 of the trocar 140. The bevel 164 may have an angle of from 180 degrees to 5 degrees and including from 50 degrees to 35 degrees. The bevel 164 may have geometry consisting of multiple bevels, angles, and undulating surfaces to provide the desired shapes for sample ejection. A distal end 165 of the bevel 164 may be curved to form a spade shovel shaped profile. An upper surface 166 of the bevel 164 may be planar. A bottom surface 167 of the bevel 164 may be curved to conform to a lumen wall 159 of the trocar 140. The bevel 164 may be configured to displace or dislodge a tissue sample from the channel 158 of the trocar 140 as the stylet 160 is moved from a proximally through the channel 158.

In some embodiments the proximal end portion 163 of the stylet 160 may be configured to be fixedly coupled to the stylet hub 161. The stylet 160 may be fixedly coupled to the stylet hub 161 using techniques known in the art such as bonding, welding, overmolding, etc. The outside surface of the proximal end portion 163 of the stylet 160 may be modified to enhance the coupling of the stylet 160 to the stylet hub 161. For example, the surface may be chemically or mechanically etched or textured to roughen the surface in order to enhance the adhesion of an adhesive or plastic.

Alternatively, the surface may be chemically modified to enhance the adhesion of the adhesive or plastic.

The stylet hub 161 may comprise a stylet coupling portion 168, at least one elongated rail 169 and a push tab 170. The stylet hub 161 may be configured to be at least partially disposed within the cavity 147 of the trocar hub 141. The coupling portion 168 may be cylindrical in shape with a bore 174 sized to accommodate the proximal end portion 163 of the stylet 160. The proximal end portion 163 may be fixedly coupled to the coupling portion 168 as described above. The elongated rails 169 may extend distally from a proximal end portion 171. The elongated rails 169 may be configured to be disposed within the housing base 180. Guide rails 184 within the housing base 180 may be configured to cooperate with the rails 169 to guide the stylet hub 161 along the longitudinal axis of the actuator 108. The push tab 170 may be configured to radially extend from the coupling portion 168. The push tab 170 may be configured to allow for application of both a proximally directed force and a distally directed force from a practitioner's finger or thumb. The push tab 170 may comprise a proximally facing inclined surface 172 and a distally facing inclined surface 173. The inclined surfaces 172, 173 may be configured to conform to the finger or thumb of the practitioner to facilitate both proximal and distal movement of the stylet assembly 106. The stylet hub 161 may be formed from an opaque or translucent plastic material using manufacturing techniques known to the industry such as injection molding, casting, machining, etc.

Figure 6:
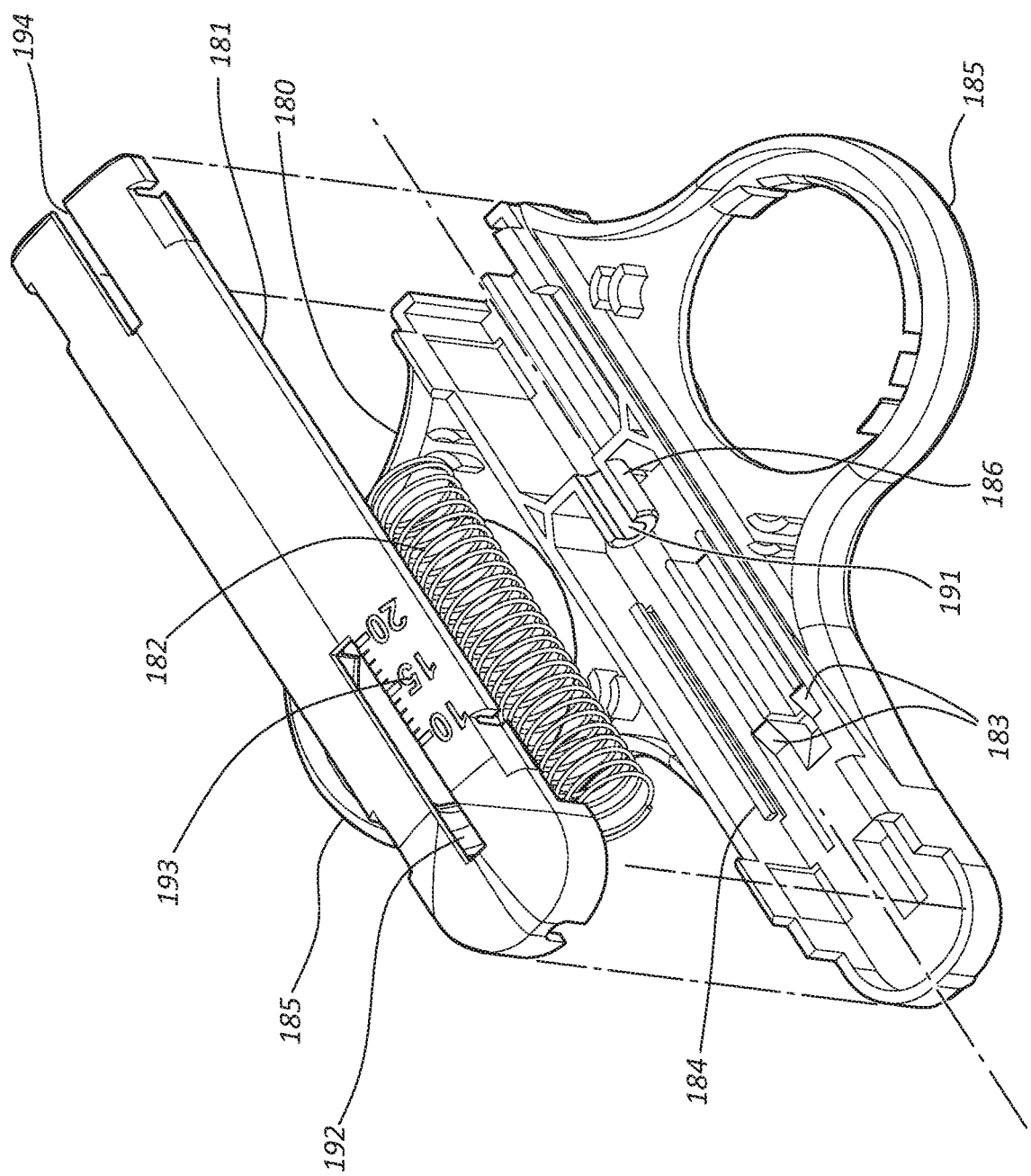
FIG. 6 is a perspective view of a housing base of the biopsy needle device of FIGS. 1 and 2.

FIG. 6 is an exploded perspective view the housing base 180 of the actuator 108 and the housing lid 181 of the actuator 108. Referring now to FIG. 6, in some embodiments the housing base 180 may comprise a body 187, finger grips 185, locking teeth 183, a spring support 186 and guide rails 184. The finger grips 185 may extend laterally from the body 187. The finger grips 185 may be configured as full circles or truncated circles to accommodate the fingers of a practitioner. The finger grips 185 may be formed from a rigid plastic with a soft plastic material overlaying portions of the rigid plastic to enhance gripability and comfort. Alternatively, the finger grips 185 may be configured as any other embodiment known in the industry that may facilitate ease of handling and manipulation of the biopsy needle device 100.

In some embodiments the locking teeth 183 of the housing base 180 may be configured to engage with the locking teeth 130 of the cannula hub 121. The engagement of the locking teeth 183, 130 may facilitate the cocking of the actuator 108 and the locking of the cannula assembly 102 in a selected proximal location. The guide rails 184 may extend upward from the floor 189 of the housing base 180. The guide rails 184 may cooperate with the actuation extension 149 of the trocar hub 141 and the rails 169 of the stylet hub 161 to guide both distal and proximal movements of the trocar assembly 104 and the stylet assembly 106. The spring support 186 may extend distally from a wall 190 positioned proximal of the cannula hub 121 when the cannula hub 121 is disposed within the housing base 180. The spring support 186 may be cylindrical with a bore 191 configured to permit passage of the trocar 140 and the stylet 160. The outer diameter of the spring support 186 may be configured to fit a coiled spring 182 over the spring support 186. The housing base 180 may furthermore comprise a coiled type compression spring 182 configured to apply a distally directed force to the cannula hub assembly 102. The proximal end of the spring 182 may fit over the spring support 186 and the distal end of the spring 182 may fit in the cavity 129 of the cannula hub 121. The housing base 180 may be formed from an opaque or translucent plastic material using manufacturing techniques known to the industry such as, injection molding, casting, machining, etc.

The housing lid 181 may comprise a window 192, indicia 193 and a longitudinal slot 194. The window 192 may be rectangular in shape with the long axis being parallel to the longitudinal axis of the actuator 108. The window 192 may be configured to permit the practitioner to see the location of the cannula hub 121 when cocking the actuator 108. In addition to cocking the actuator 108, the practitioner may utilize the window 192 and the indicia 193 located along the window 192 to select a tissue sample length that may be collected during the biopsy procedure. For example, the cannula hub 121 may be moved proximally by the practitioner as the actuator 108 is cocked. The practitioner may observe the location of the distal end 133 of the cannula hub 121 through the window 192 and thereby know the location of the distal end 133 with respect to the device. The indicia 193 may indicate millimeters of tissue sample length, for example 10 millimeters, 15 millimeters or 20 millimeters. When the distal end 133 lines up with the desired indicium 193, the practitioner may stop cocking the actuator 108 and the cannula assembly 102 may be locked in position. The slot 194 may be located in the proximal end portion of the housing lid 181. The slot 194 may be configured to permit distal and proximal movement of the stylet assembly 106. The housing lid 181 may be configured to fit over the housing base 180. The housing lid 181 may be coupled to the housing base 180 utilizing assembly techniques known in the industry. For example, the housing lid 181 may be coupled to the housing base 180 using a snap fit, adhesive, welding, etc. The housing lid 181 may be formed from an opaque or translucent plastic material using manufacturing techniques known to the industry such as injection molding, casting, machining, etc. The indicia 193 may be applied to the housing lid 181 utilizing techniques such as transfer printing, laser printing, labels, etc.

Figure 12:
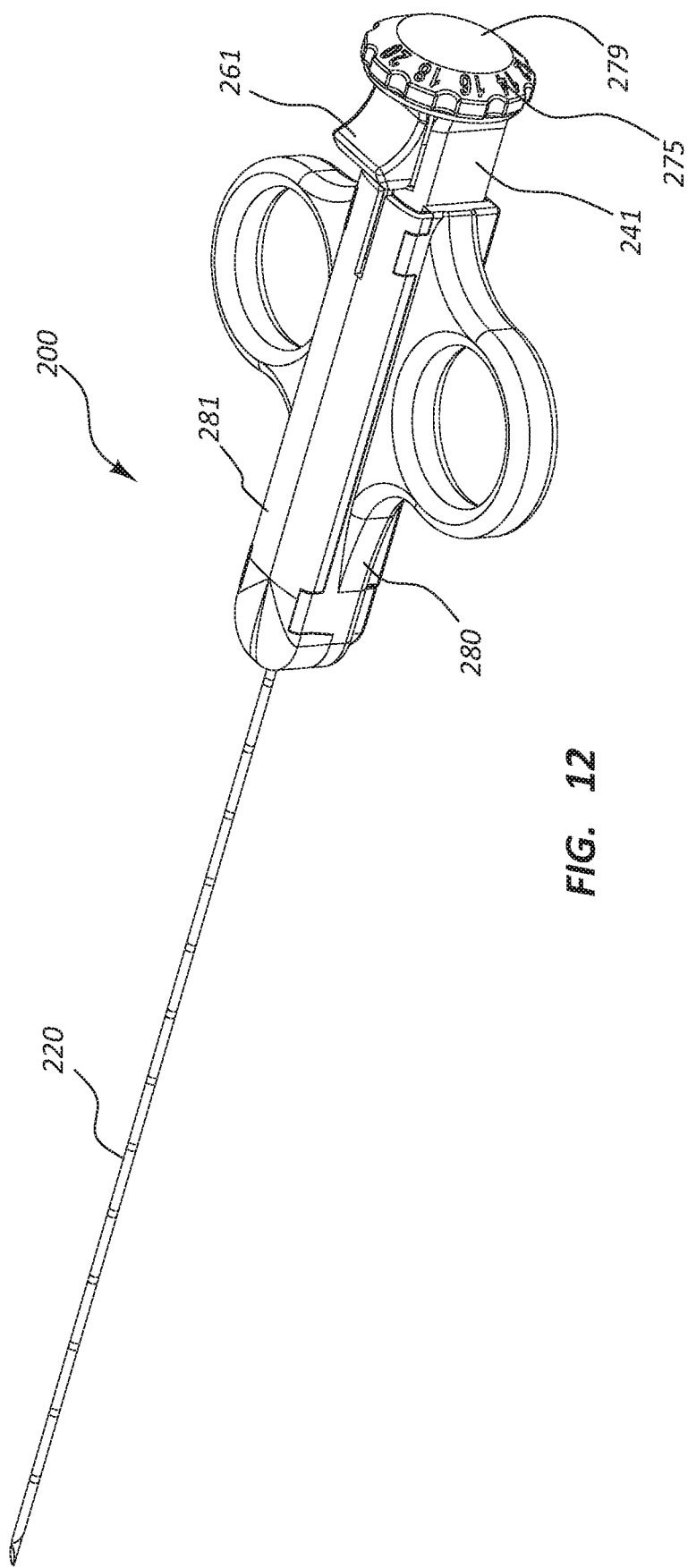
FIG. 12 is a perspective view of a biopsy needle device having a dial selector.
Figure 13:
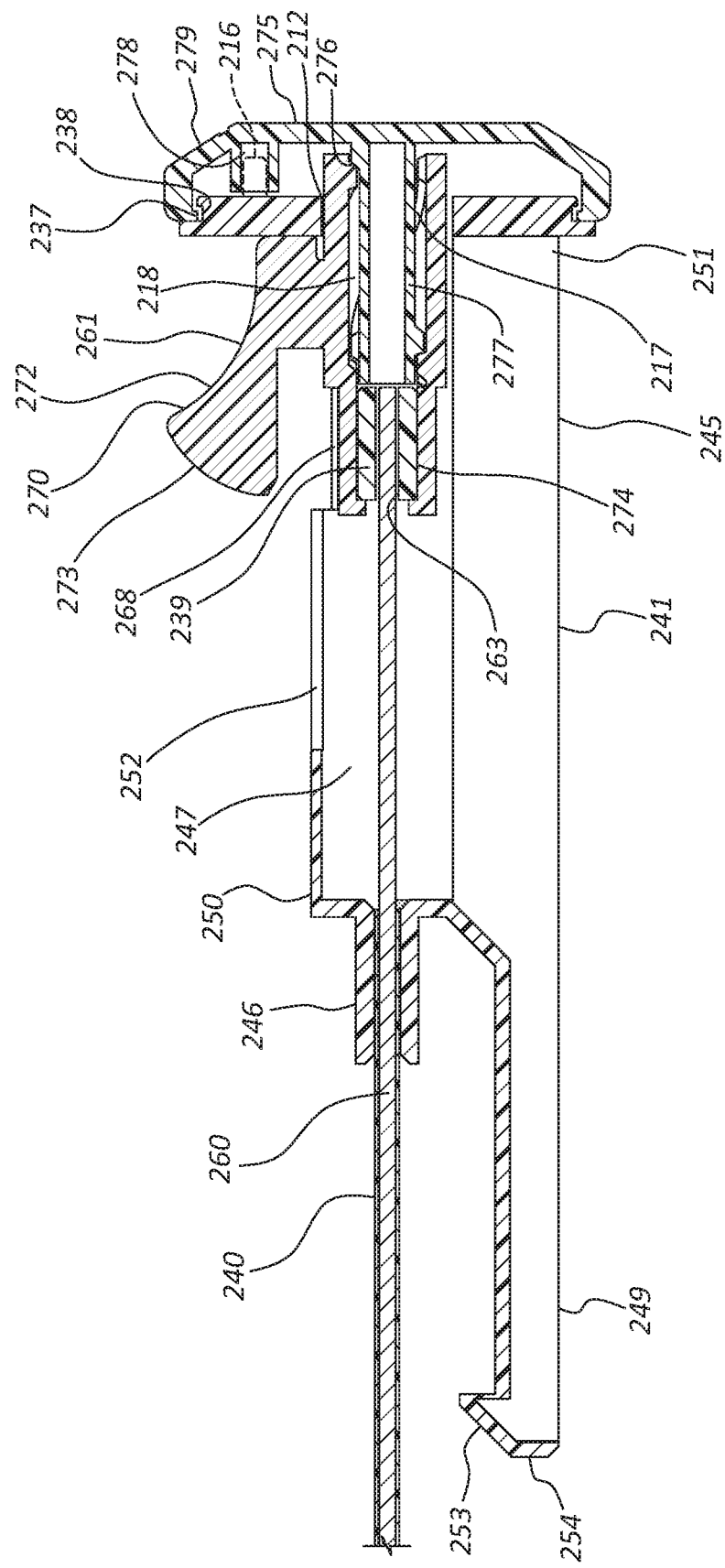
FIG. 13 is a cross-sectional view of portions of the biopsy needle device of FIG. 12.

FIGS. 12 and 13 illustrate a biopsy needle device 200. Biopsy needle device 200 may be analogous to biopsy needle device 100 as illustrated in FIGS. 1-11A with a dial selector 279 positioned at the proximal end of the biopsy needle device 200 which will be described in detail below. FIG. 12 is a perspective view of biopsy needle device 200. FIG. 13 is a cross-sectional view of portions of the biopsy needle device 200 of FIG. 12.

As illustrated in FIGS. 12 and 13, biopsy needle device 200 comprises a cannula 220, a cannula hub 221 (not shown), a housing base 280, a stylet 260 and a trocar 240, all of which may be interchangeable with like components of the biopsy needle device 100. Additionally, biopsy needle device 200 comprises a trocar hub 241, a stylet hub 261, a housing lid 281 and the dial selector 279.

Referring to FIG. 13, in some embodiments, the trocar hub 241 may comprise a body 245, a trocar coupling portion 246, a cavity 247, a proximal flange 210 and an actuation extension 249. The trocar hub 241 may be disposed within the proximal end portion of the housing base 280 and be configured to move along a longitudinal axis of the housing base 280. The trocar coupling portion 246 may be generally cylindrical with a diameter to accommodate the trocar 240 and a length to provide a secure coupling of the trocar 240 to the trocar coupling portion 246. The trocar coupling portion 246 may be positioned near a distal end 250 of the body 245 of the trocar hub 241. The cavity 247 may extend from the distal end 250 of the body 245 to a proximal end 251 of the body 245. The cavity 247 may be configured to accommodate a portion of the stylet hub 261. The body 245 may further comprise a longitudinal slot 252 configured to allow for distal and proximal movement of the stylet hub 261. The actuation extension 249 of the trocar hub 241 may extend distally from the body 245. The actuation extension 249 may comprise a hook member 253 at a distal end 254. The hook member 253 may be configured to engage a shoulder of the cannula hub 221 such that proximal movement of the trocar hub 241 may result in proximal movement of the cannula hub 220. Additionally, the hook member 253 may be configured to engage with the cannula hub 221 such that the cannula hub 221 may be disengaged from a locked position within the housing base 280 allowing for the cannula hub 221 to move distally. The flange 210 may be located at the proximal end 251 of the body 145. The flange 210 may be configured for rotatable coupling of the dial selector 279 to the flange 210. The flange 210 may comprise a central passage 212, a circumferential groove 213 configured for coupling of the dial selector 279 and a selector post 216. The trocar hub 141 may be formed from an opaque or translucent plastic material using manufacturing techniques known to the industry such as injection molding, casting, machining, etc.

The dial selector 279 may be a concave disc. The dial selector may comprise indicia 275 located on the proximal face of the dial selector 279. The indicia 275 may be configured to indicate to the practitioner the length of a tissue sample to be collected. The indicia 275 may be molded, printed, labeled or any other acceptable technique known in the art may be used to apply the indicia onto the dial selector 279. The dial selector 279 may further comprise a radially, inwardly extending ring 237 configured to engage the groove 213 of the cannula hub 221. The engagement of the ring 237 and the groove 213 may be configured to couple the dial selector 279 to the flange 210 such that the dial selector 279 may rotate around a central axis.

In some embodiments, the dial selector 279 may also comprise a selector channel 278. The selector channel 278 may be configured with a smooth inner wall 214 and a scalloped outer wall 215. The channel may be configured to engage the selector post 216 projecting proximally from the distal face of the flange 210. The diameter of the selector post 216 may be configured to be approximately equivalent to wide portions of the channel 278 and to be larger than narrow portions of the channel 278. The wide portions of the channel 278 may correspond to the indicia 275 such that the selector dial 279 may be positioned at discreet rotational locations. Rotational movement of the selector dial 279 from one discreet location to another may require an additional rotational force applied by the practitioner due to the diameter of the selector post 216 being larger than the narrow portions of the channel 278. The dial selector 279 may further comprise a distally extending protrusion 217. The protrusion 217 may comprise an external thread 277 configured to engage an internal thread 276 of the stylet hub 261.

The stylet hub 261 may comprise a stylet coupling portion 268, a cavity 218 and a push tab 270. The stylet hub 261 may be configured to be at least partially disposed within the cavity 247 of the trocar hub 241. The coupling portion 268 may be cylindrical in shape with a bore 274 sized to accommodate a plug 239. The plug may be cylindrical in shape and may surround a proximal end portion 263 of the stylet 260. The proximal end portion 263 may be fixedly coupled to the plug 239 utilizing techniques known in the art, such as insert molding, bonding, welding, etc. The plug may be positioned within the bore 274 and retained using techniques known in the art such as press fit, bonding, welding, etc. The push tab 270 may be configured to radially extend from the stylet hub 261. The push tab 270 may be configured to allow for application of both a proximally directed force and a distally directed force from a practitioner's finger or thumb. The push tab 270 may comprise a proximally facing inclined surface 272 and a distally facing inclined surface 273. The inclined surfaces 272, 273 may be configured to conform to the finger or thumb of the practitioner to facilitate both proximal and distal movement of the stylet hub 261. The proximal end of the stylet hub 261 may extend proximally through the passage 212. The protrusion 217 may extend into the cavity 218. The cavity 218 may comprise the internal thread 276 configured to engage the external thread 277 of the protrusion 217. The periphery of the dial selector 279 may comprise grip enhancing features, such as knurls, ribs, bumps, dimples, etc.

The practitioner may utilize the dial selector 279 to displace the stylet hub 261 and the stylet 260 both distally and proximally a desired distance. The practitioner may rotate the dial selector 279 such that a selected indicium 275 may be aligned with the top of the biopsy needle device 200. The selected indicium 275 may correlate with the desired tissue sample length to be collected. The rotation of the dial selector 279 may engage the internal thread 276 and the external thread 277 such that the stylet hub 261 may be displace distally or proximally dependent upon the direction of rotation of the dial selector 279. The distal end of the stylet 260 may be displaced as the dial selector 279 may be rotated to a selected indicium 275. The distal end of the stylet may be located at discreet locations within the notch 257 and/or channel 258 of the trocar 240 such that the stylet 240 may fill a portion of the notch and/or channel and a tissue sample may fill the remainder of the notch 257 and/or channel. The stylet hub 261 may be decoupled from the dial selector 279 such that the stylet hub 261 may be positioned in a distal location. The stylet hub 261 may be re-coupled to the dial selector 279.

In some embodiments, an introducer cannula (not shown) may be used with the biopsy needle devices 100, 200 disclosed herein. The introducer cannula may comprise an outer cannula sized to permit passage of the biopsy needle, a trocar slidably positioned within the cannula and extending beyond the distal end of the cannula, and a depth stop to facilitate positioning of the introducer at the desired insertion depth. In use with the biopsy needle devices 100, 200, the introducer cannula assembly may be inserted into a patient's tissue with the distal end of the introducer cannula positioned adjacent to the targeted tissue. The depth stop may be used to restrict insertion depth to a predetermined depth. The trocar may be removed. A portion of the biopsy needle devices 100, 200 may be inserted through the introducer cannula and into the targeted tissue. A tissue sample may be severed from the targeted tissue and retained within the biopsy needle devices 100, 200. The biopsy needle devices 100, 200 may be withdrawn from the targeted tissue and the introducer cannula. The tissue sample may be extracted from the biopsy needle devices 100, 200. If additional tissue samples are desired from the same target tissue, the process may be repeated. The introducer cannula may be removed from the patient when all desired tissue samples have been collected.

FIGS. 7-11A are schematic in nature. In other words, the figures show the functional and operational relationships of portions of the biopsy needle device 100 upon use in a patient, but the figures are not intended to indicate any particular structure or spatial disposition of any tissue, organ, body component, or group of body components in the patient. Additionally, the schematic representations herein may be drawn to show internal tissues and/or organs of the patient without explicitly designating cross-sections or cut-aways of the tissues and/or organs. For example, a body tissue may be schematically shown with the biopsy needle device 100 disposed therein without indicating a cross-section portion or cutaway of a portion of the body tissue.

Figure 7:
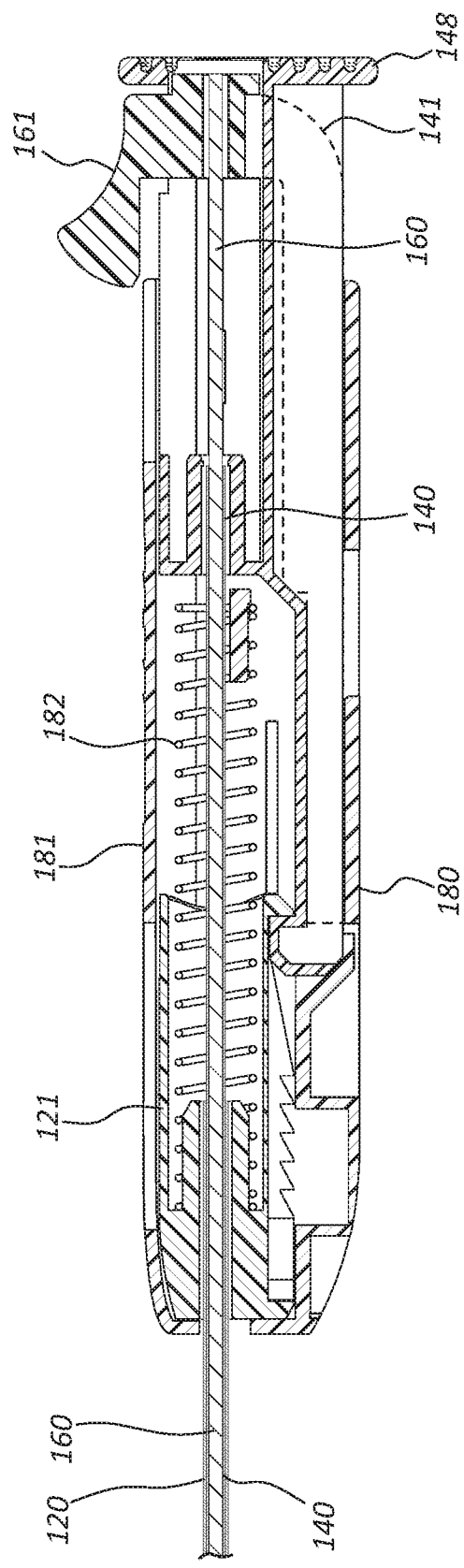
FIG. 7 is a schematic cross-sectional representation of portions of the biopsy needle device of FIGS. 1 and 2 in a first configuration.
Figure 7A:
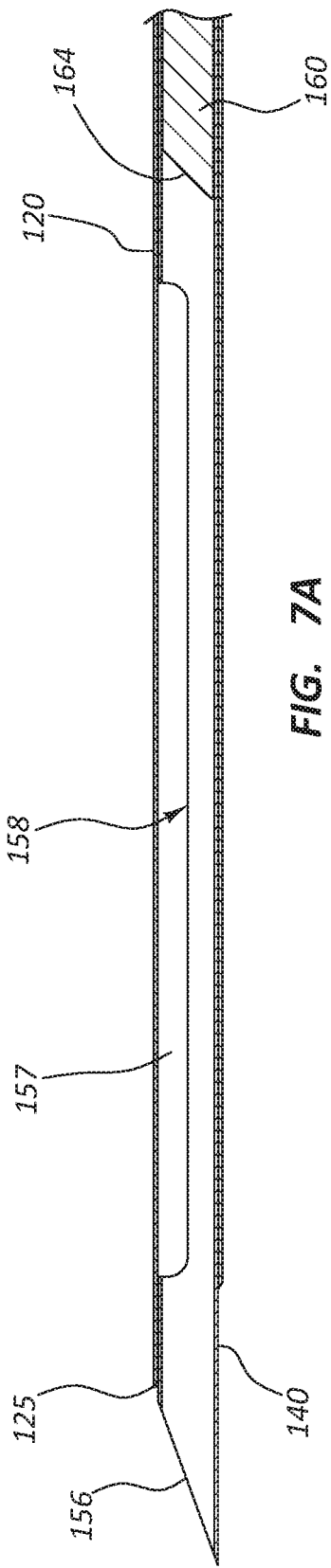
FIG. 7A is a schematic cross-sectional representation of portions of the cannula, the trocar and the stylet of the biopsy trocar device of FIG. 7 in the first configuration shown in FIG. 7.
Figure 10:
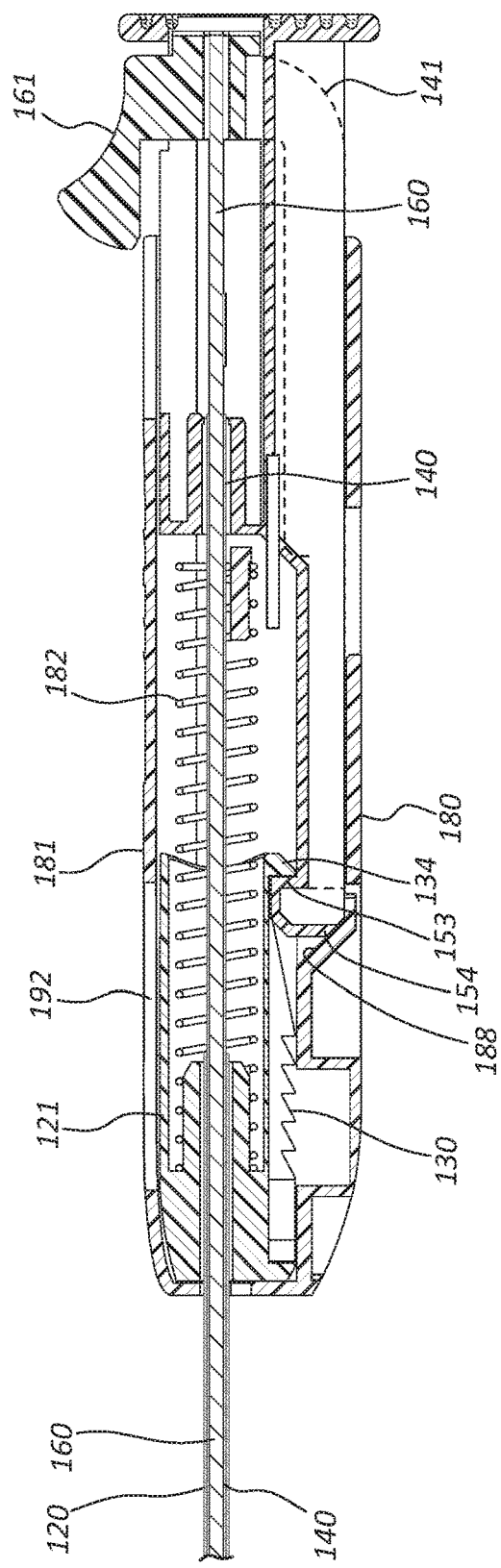
FIG. 10 is a schematic cross-sectional representation of portions of the biopsy needle device of FIGS. 1 and 2 in a fourth configuration.
Figure 10A:
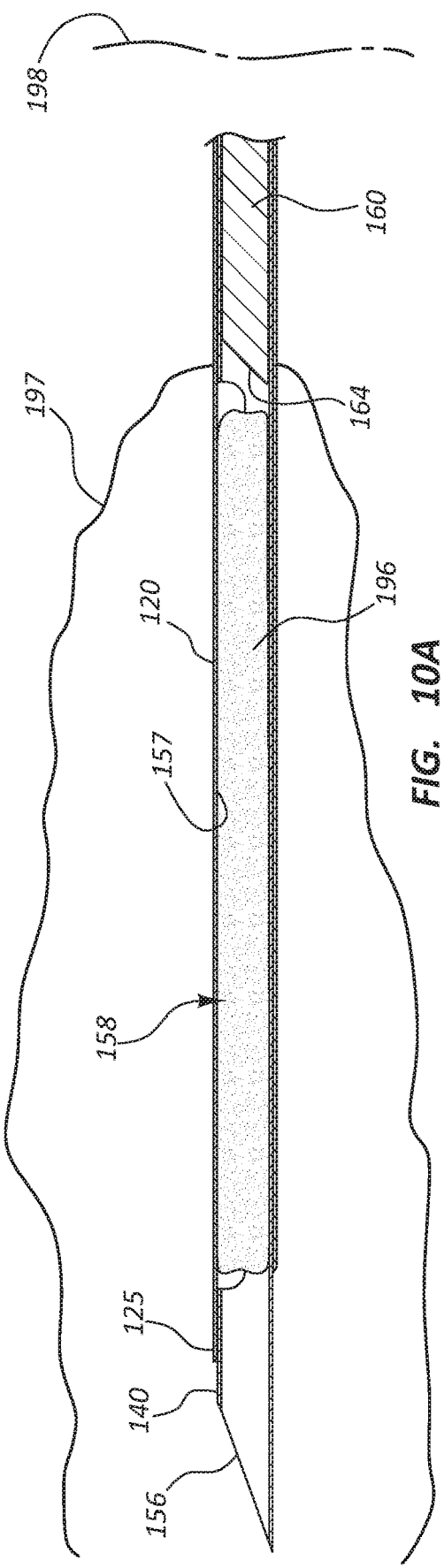
FIG. 10A is a schematic cross-sectional representation of portions of the cannula, the trocar and the stylet of the biopsy needle device of FIG. 10 in the fourth configuration shown in FIG. 10.

FIGS. 7 and 7A are cross-sectional schematic representations of a side view of portions of the biopsy needle device 100 of FIG. 1 in a first configuration. FIGS. 8 and 8A are cross-sectional schematic representations of a side view of portions of the biopsy needle device 100 of FIG. 1 in a second configuration. FIGS. 9 and 9A are cross-sectional schematic representations of a side view of portions of the biopsy needle device 100 of FIG. 1 in a third configuration. FIGS. 10 and 10A are cross-sectional schematic representations of a side view of portions of the biopsy needle device 100 of FIG. 1 in a fourth configuration. FIGS. 11 and 11A are cross-sectional schematic representations of a side view of portions of the biopsy needle device 100 of FIG. 1 in a fifth configuration.

FIG. 7 illustrates the relative locations of the cannula hub 121, the trocar hub 141 and the stylet hub 161 within the actuator 108 in a first configuration. The first configuration may be prior to cocking of the actuator 108 by the practitioner. As can be seen, the cannula hub 121 may be positioned at the distal end portion of the housing base 180. The trocar hub 141 may be positioned at a distal position wherein the actuation pad 148 may be proximal to the housing base 180. The stylet hub 161 may be positioned in an intermediate position such that the push tab 170 may be between the proximal end of the housing base 180 and the actuation pad 148 of the trocar hub 141.

FIG. 7A illustrates portions the cannula 120, the trocar 140 and the stylet 160 of the trocar assembly 104 in the first configuration. As can be seen, the trocar bevel 156 may extend beyond the distal end of the cannula 120. The distal end of the cannula 120 may be located between the trocar bevel 156 and the notch 157, i.e., the distal end of the cannula 120 may be proximal to the trocar bevel 156 and distal to the notch 157. The distal end of the stylet 160 may be located proximal to the notch 157 and/or channel 158.

FIG. 8 illustrates the relative locations of the cannula hub 121, the trocar hub 141 and the stylet hub 161 within the actuator 108 in a second configuration. The second configuration may be achieved following cocking of the actuator 108 and following insertion of the cannula 120, the trocar 140 and the stylet 160 into the tissue of the patient. As can be seen, the cannula hub 121 may be in a selected proximal position. The locking teeth 130 of the cannula hub 121 may be engaged with the locking teeth 183 of the housing base 180. The hook member 153 of the trocar hub 141 may be engaged with the shoulder 134 of the cannula hub 121 to displace the cannula hub 121 to the selected proximal position. The practitioner may have predetermined the tissue sample length to be collected and then observed the location of the distal end 133 of the cannula hub 121 relative to the indicia 193. The practitioner may stop cocking the actuator 108 and moving the trocar hub proximally when he/she observes the distal end portion 150 of the cannula hub 121 may be lined up with the desired tissue sample length indicium 193. The trocar hub 141 and the stylet hub 161 may be positioned proximally from the first configuration (FIG. 7).

FIG. 8A illustrates portions of the cannula 120, the trocar 140 and the stylet 160 of the biopsy needle device 100 in the second configuration. As can be seen, the bevel 156 of the trocar 140 may extend beyond the distal end of the cannula 120. The bevel may be through the skin 198 and adjacent to a periphery of a target tissue or lesion 197. The distal end of the cannula 120 may be located between the bevel 156 and the notch 157, i.e., the distal end of the cannula 120 may be proximal to the bevel 156 and distal to the notch 157. Also, the distal end of the stylet 160 may be located proximal to the notch 157 and/or channel 158. Alternatively, the distal end of the stylet may be located adjacent to and proximal to the bevel 156.

FIG. 9 illustrates the relative locations of the cannula hub 121, the trocar hub 141 and the stylet hub 161 within the actuator 108 in a third configuration. The third configuration may be achieved following insertion of the trocar 140 into the target tissue or lesion 197. As can be seen, the cannula hub 121 may be in a selected proximal position. The locking teeth 130 of the cannula hub 121 may be engaged with the locking teeth 183 of the housing base 180. The trocar hub 141 may be in the distal position. The stylet hub 161 may be in the intermediate position. In certain embodiments the stylet hub 161 may be advanced distally an additional distance to a selected distal position such that the stylet hub 161 is positioned within the slot 194 of the housing lid 181.

FIG. 9A illustrates portions of the cannula 120, the trocar 140 and the stylet 160 of the biopsy needle device 100 in the third configuration. As can be seen, the distal end portion 142 of the trocar 140, including the bevel 156 and the notch 157 and/or channel 158, may extend beyond the distal end of the cannula 120. The distal end of the cannula 120 may be located proximal to the notch 157 and/or channel 158 and may be positioned at the perimeter of the target tissue or lesion. Alternatively, in some embodiments the distal end portion 122 of the cannula 120 may partially extend over and may partially cover the notch 157 and/or channel 158. The position of the distal end portion 122 of the cannula 120 relative to the notch 157 and/or channel 158 may be determined by the practitioner as he/she cocks the actuator 108 and sets the position of the cannula hub 121 relative to the indicia 193 of the housing lid 181. The position of the distal end portion 122 of the cannula 120 may determine the length of the tissue sample collected. For example, the distal end portion 122 may be positioned proximal of the notch 157 and/or channel 158 as illustrated in FIG. 8A. In this position, the notch 157 and/or channel 158 may be fully to exposed the target tissue or lesion 197 resulting in the collection of a tissue sample 196 having a length of the notch 157 and/or channel 158. Alternatively, the distal end portion 122 of the cannula 120 may be positioned over one half or any other portion of the notch 157 and/or channel 158. In this position, one half of the length of the notch 157 and/or channel 158 or any other portion may be exposed to the target tissue or lesion 197 resulting in a tissue sample 196 equivalent of the length of the exposed notch 157 and/or channel 158.

In some embodiments the distal end of the stylet 160 may be located proximal to the notch 157 and/or channel 158 in the third configuration. Alternatively, the distal end of the stylet 160 may be positioned proximal to and adjacent to the distal end of the trocar 140. In this position, the stylet 160 may be configured to provide added stiffness to the trocar 140 and increase pushability or the ability of the trocar 140 to penetrate a dense or calcified tissue sample or lesion 197 without the trocar 140 bending in the area of the notch 157 and/or channel 158. In some embodiments the stylet 160 may be used to collect a desired tissue sample length. Following insertion of the trocar 140 into the target tissue or lesion, the distal end of the stylet 160 may be positioned at a desired location within the notch 157. The position of the stylet 160 may be determined rotation of a selector 279. The stylet 160 may fill a portion of the notch 157 and/or channel 158 proximal to the distal end of the stylet 160 such that tissue will not collapse into the notch 157 and/or channel 158. A portion of the notch 157 and/or channel 158 may be open distal of the distal end of the stylet 160 allowing tissue to collapse into the notch 157 and/or channel 158 and fill the notch 157 and/or channel 158 with tissue.

FIG. 10 illustrates the relative locations of the cannula hub 121, the trocar hub 141 and the stylet hub 161 within the actuator 108 in a fourth configuration. The fourth configuration may be achieved following actuation of the actuator 108 and cutting or severing of the tissue sample 196. As can be seen, the cannula hub 121 may be moved by decompression of the spring 182 from a locked proximal position (FIGS. 8 and 9) to a fully distal position within the actuator 108. The practitioner may apply a distally directed force to the actuation pad 148 of the trocar hub 141 such that the trocar hub 141 may move distally an additional distance. The distal end 154 of the actuation extension 149 of the trocar hub 141 may engage a ramp 188 of the housing base 180. The ramp 188 may direct the hook member 153 of the trocar hub 141 against the bottom surface of the cannula hub 121 and locking teeth 183 resulting in the release of the cannula hub 121 and disengagement of the locking teeth 130 of the cannula hub 121 from the locking teeth 183 of the housing base 180. Upon disengagement, the spring 182 may be allowed to decompress and move the cannula hub 121 distally.

FIG. 10A illustrates portions of the cannula 120, the trocar 140 and the stylet 160 of the biopsy needle device 100 in the fourth configuration. As can be seen, the bevel 156 of the trocar 140 may extend beyond the distal end of the cannula 120. The distal end of the cannula 120 may be located between the bevel 156 and the notch 157 and/or channel 158, i.e., the distal end of the cannula 120 may be proximal to the bevel 156 and distal to the notch 157 and/or channel 158. The distal end of the stylet 160 may be located proximal to the notch 157 and/or channel 158. In some embodiments the distal end of the stylet 160 may be positioned within the notch 157 and/or channel 158 such that the tissue sample 196 may only fill a portion of the notch 157 distal to the distal end of the notch 157 and/or channel 158.

FIG. 11 illustrates the relative locations of the cannula hub 121, the trocar hub 141 and the stylet hub 161 within the actuator 108 in a fifth configuration. The fifth configuration may be achieved following removal of the biopsy needle device 100 from the patient and extraction of the collected tissue sample. As can be seen, the cannula hub 121 may be in a fully proximal position. The locking teeth 130 of the cannula hub 121 may be engaged with the locking teeth 183 of the housing base 180. The trocar hub 141 may be in a distal position. The stylet hub 161 may be in a full distal position. The stylet hub 161 may be advanced distally such that the stylet hub 161 may be positioned within the slot 194 of the housing lid 181.

FIG. 11A illustrates portions of the cannula 120, the trocar 140 and the stylet 160 of the biopsy needle device 100 in the fifth configuration. As can be seen, the distal end portion 142, including the bevel 156 and the notch 157 and/or channel 158, of the trocar 140 may extend beyond the distal end of the cannula 120 such that the notch 157 and/or channel 158 may be exposed. The distal end of the stylet 160 may be positioned adjacent to and proximal to the distal end of the trocar 140. Movement of the stylet 160 from the proximal position of FIG. 10A to the distal position of FIG. 11A may result in the displacement or dislodgement of the collected tissue sample from the notch 157 and/or channel 158.

The biopsy needle device 100 may permit the practitioner to perform the Core Needle Biopsy procedure utilizing a semi-automatic technique and to extract a tissue sample from the biopsy needle device 100 utilizing the integrated stylet 160. The location of the tissue or lesion to be biopsied within the patient may be identified utilizing known diagnosis techniques such as computed tomography, magnetic resonance imaging, x-ray, ultrasound, etc. The patient may be positioned and prepped for the Core Needle Biopsy procedure. The practitioner may obtain the sterilized biopsy needle device 100 configured with the desired length and diameter. The practitioner may cock the actuator 108 by utilizing the push tab 170 to move the cannula assembly 102, the trocar assembly 104 and the stylet assembly 106 proximally. The practitioner may select the distance the actuator 108 is cocked according to the desired length of tissue to be biopsied. The practitioner may insert the cannula 120, the trocar 140 and the stylet 160 through the skin and into the tissue of the patient while holding the actuator 108 in a hand. Alternatively, the cannula 120, the trocar 140 and the stylet 160 may be inserted into the tissue of a patient utilizing an introducer cannula that was previously inserted into the patient. The trocar 140 may be inserted until the distal end of the trocar 140 may be adjacent to the perimeter of the target tissue or lesion. The trocar 140 may be inserted into the target tissue or lesion such that at least a portion of the notch 157 and/or channel 158 may be surrounded by the target tissue and/or lesion tissue. The distal end portion 122 of the cannula 120 may cover a portion of the notch 157 and/or channel 158. Alternatively, the trocar 140 and the stylet 160 may jointly be inserted into the target tissue or lesion whereby the stylet 160 may increase the pushability of the trocar 140 into the target tissue or lesion without bending of the trocar 140 in the area of the notch 157 and/or channel 158. The practitioner may confirm the position of the distal end portion 142 of the trocar 140 utilizing known techniques such as ultrasound, computed tomography, x-ray, etc. A portion of the target tissue or lesion may collapse into the notch 157 and/or channel 158. The distal end of the stylet 160 may be positioned proximally of the notch 157 and/or channel 158. Alternatively, the distal end of the stylet 160 may be positioned within the notch 157 and/or channel 158 such that a desired length of tissue collapses into the notch 157 and/or channel 158. The practitioner may activate the actuator 108 by applying a distally directed force to the actuation pad 148 of the trocar hub 141 resulting in the cannula assembly 102 becoming unlocked and advancing distally. The distal end portion 122 of the cannula 120 may slide over the notch 157 and/or channel 158 of the trocar 140 and cut or sever the tissue sample within the notch 157 and/or channel 158 from the surrounding target tissue or lesion tissue. The tissue sample may be captured and retained within the notch 157 and/or channel 158 by the cannula 120. The cannula 120, the trocar 140 and the stylet 160 may be removed from the patient's tissue. The cannula assembly 102 may be moved proximally and locked in position such that that the distal end of the cannula 120 may be positioned proximally of the notch 157 and/or channel 158. The practitioner may apply a distally directed force to the push tab 170 of the stylet hub 161 resulting in distal movement of the distal end portion 162 of the stylet 160. The bevel 164 of the stylet 160 may displace or dislodge the collected tissue sample from the notch 157 and/or channel 158. The tissue sample may be analyzed using known techniques.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A biopsy needle device, comprising:
   a cannula comprising a beveled distal end configured to sever a tissue sample;
   a trocar disposed within the cannula comprising an open beveled distal end and a notch configured to retain a tissue sample, wherein the notch is disposed proximal to a distal end of the trocar, wherein the trocar is hollow, and wherein the notch extends a length along the trocar from a proximal end of the notch to a distal end of the notch, wherein the length of the notch is greater than a width of the notch, and wherein the notch further comprises an open channel having a semi-circular wall with a length of the open channel greater than a width of the open channel; and
   a stylet disposed within the trocar comprising a distal end configured to dislodge the tissue sample from the notch, wherein the distal end of the stylet comprises a bevel, and
   wherein the bevel comprises:
   a curved distal end to form a spade shovel shaped profile; a planar upper surface; and
   a curved bottom surface to conform to a lumen wall of the trocar.

2. The biopsy needle device of claim 1, further comprising an actuator wherein the actuator comprises:
   a cannula hub configured to be coupled to the cannula; a trocar hub configured to be coupled to the trocar; and a stylet hub configured to be coupled to the stylet.

3. The biopsy needle device of claim 2, wherein the stylet hub is coupled to a selector configured to displace the stylet hub distally and/or proximally.

4. The biopsy needle device of claim 2, wherein the cannula hub is configured to lock into at least one of multiple discreet positions within the actuator.

5. The biopsy needle device of claim 1, wherein a channel is formed between the opened beveled distal end and the notch.

6. The biopsy needle device of claim 2, wherein the actuator further comprises an energy storage member configured to displace the cannula hub from a proximal position to a distal position.

7. The biopsy needle device of claim 6, wherein the energy storage member is a compression spring.

8. The biopsy needle device of claim 2, wherein the actuator further comprises a housing.

9. The biopsy needle device of claim 8, wherein the housing comprises locking teeth configured to engage locking teeth of the cannula hub to lock the cannula hub in a ready position.

10. The biopsy needle device of claim 9, wherein the trocar hub comprises a hook member configured to engage the cannula hub to displace the cannula hub to the ready position and configured to release the cannula hub from the ready position.

11. The biopsy needle device of claim 8, wherein the housing further comprises a window configured to permit visualization of the cannula hub.

12. The biopsy needle device of claim 1, wherein the cannula is configured to slide distally and proximally over the trocar.

13. The biopsy needle device of claim 1, wherein the cannula further comprises at least one indicium.

14. A method of collecting a tissue sample: comprising, obtaining a biopsy needle device comprising:
   a cannula comprising a beveled distal end configured to sever the tissue sample;
   a trocar disposed within the cannula comprising an open beveled distal end and a notch configured to retain the tissue sample, wherein the notch is disposed adjacent a distal end of the trocar, and wherein the trocar is hollow such that a channel is formed between the opened beveled distal end and the notch;
   a stylet disposed within the trocar configured to dislodge the tissue sample; and
   an actuator wherein the cannula, the trocar and the stylet are operably coupled to the actuator;
   cocking the actuator such that a distal end of the cannula is locked in a position that at least partially covers the notch;
   inserting the cannula, the trocar and the stylet into a tissue of a patient such that a distal end of the trocar is adjacent to a lesion;
   inserting the trocar into the lesion such that at least a portion of the notch is within the lesion and the tissue sample collapses into the portion of the notch within the lesion; activating the actuator wherein the cannula slides distally over the trocar such that the portion of the tissue sample is severed and collected in the notch; removing the cannula, the trocar and the stylet from the patient; and distally sliding the stylet within the notch such that the tissue sample is extracted from the notch, wherein a distal end of the stylet comprises a bevel, and wherein the bevel comprises:

a curved distal end to form a spade shovel shaped profile; a planar upper surface; and a curved bottom surface to conform to a lumen wall of the trocar.

15. The method of collecting a tissue sample of claim 14, wherein a selected length of the notch is exposed to the lesion such that a selected length of the tissue sample collapses into the notch.

16. The method of collecting a tissue sample of claim 14, wherein the distal end of the stylet is at a selected position within the notch such that at least a portion of the notch is filled with the stylet.

17. The method of collecting a tissue sample of claim 16, wherein the selected position of the distal end of the stylet within the notch is determined by a selector coupled to a stylet hub.

18. The method of collecting a tissue sample of claim 17, further comprising:

positioning the distal end of the stylet adjacent to the distal end of the trocar;

inserting the trocar and the stylet into the lesion; and retracting the stylet a selected distance utilizing the selector such that the distal end of the stylet is positioned within the notch wherein a selected length of the tissue sample collapses into the portion of the notch not filled by the stylet.

19. A biopsy needle apparatus, comprising:

a cannula comprising a beveled distal end configured to sever a tissue sample;

a trocar comprising:

a hollow elongate tubular member;

an open beveled distal end configured to penetrate tissue; and a notch configured to retain a tissue sample, the notch extending a length along the trocar from a proximal end of the notch to a distal end of the notch, wherein the length of the notch is greater than a width of the notch, and wherein the notch further comprises an open channel having a semi-circular wall with a length of the open channel greater than a width of the open channel, and wherein the notch is disposed proximal to a distal end of the trocar; and a stylet comprising a distal end configured to dislodge a tissue sample from the channel, wherein the distal end of the stylet comprises a bevel, and wherein the bevel comprises:

a curved distal end to form a spade shovel shaped profile; a planar upper surface; and a curved bottom surface to conform to a lumen wall of the trocar.

20. The biopsy needle of claim 19, wherein the channel is configured to be slidingly coupled to a stylet such that when the stylet is displaced distally within the channel the tissue sample is radial outwardly dislodged from the channel.

* * * * *